United States Patent
Cox et al.

(10) Patent No.: US 12,157,124 B2
(45) Date of Patent: Dec. 3, 2024

(54) IMAGING SYSTEM HARDWARE

(71) Applicant: 10x Genomics, Inc., Pleasanton, CA (US)

(72) Inventors: David Maurice Cox, Foster City, CA (US); Augusto Manuel Tentori, Dublin, CA (US); Rajiv Bharadwaj, Pleasanton, CA (US)

(73) Assignee: 10x Genomics, Inc., Pleasanton, CA (US)

( * ) Notice: Subject to any disclaimer, the term of this patent is extended or adjusted under 35 U.S.C. 154(b) by 526 days.

(21) Appl. No.: 17/086,149

(22) Filed: Oct. 30, 2020

(65) Prior Publication Data

US 2021/0130881 A1     May 6, 2021

Related U.S. Application Data

(60) Provisional application No. 62/931,779, filed on Nov. 6, 2019.

(51) Int. Cl.
*B01L 3/00*      (2006.01)
*C12Q 1/6841*    (2018.01)

(52) U.S. Cl.
CPC .......... *B01L 3/5055* (2013.01); *C12Q 1/6841* (2013.01); *B01L 2200/025* (2013.01)

(58) Field of Classification Search
CPC ....... B01L 2200/025; B01L 2300/0636; B01L 2300/0819; B01L 2300/0822; B01L 2400/0605; B01L 3/5055; B01L 7/52; C12Q 1/6816; C12Q 1/6841; C12Q 2531/113; C12Q 2563/179; C12Q 2565/501; C12Q 2565/513

See application file for complete search history.

(56) References Cited

U.S. PATENT DOCUMENTS

| 4,514,388 A | 4/1985 | Psaledakis |
| 4,557,903 A | 12/1985 | McCormick |
| 4,574,729 A | 3/1986 | Wells |

(Continued)

FOREIGN PATENT DOCUMENTS

| CA | 2169928 C | * | 4/2007 | ......... A61B 10/0096 |
| CA | 3054046 |  | 3/2020 |  |

(Continued)

OTHER PUBLICATIONS

Anonymous (Jun. 15, 2018) "ST Spot Detector Usage Guide. A Guide to Using the Spatial Transcriptomics Spot Detector 2.0", GitHub, 4 pages.

(Continued)

*Primary Examiner* — Jennifer Wecker
*Assistant Examiner* — Jonathan Bortoli
(74) *Attorney, Agent, or Firm* — Fish & Richardson P.C.

(57) ABSTRACT

A sample holder includes a first member featuring a first retaining mechanism configured to retain a first substrate that includes a sample, a second member featuring a second retaining mechanism configured to retain a second substrate that includes a reagent medium, and an alignment mechanism connected to at least one of the first and second members, and configured to align the first and second members such that the sample contacts at least a portion of the reagent medium when the first and second members are aligned.

23 Claims, 19 Drawing Sheets

(56) References Cited

U.S. PATENT DOCUMENTS

| | | |
|---|---|---|
| 4,683,195 A | 7/1987 | Mullis et al. |
| 5,061,049 A | 10/1991 | Hornbeck |
| 5,183,053 A | 2/1993 | Yeh et al. |
| 5,436,129 A * | 7/1995 | Stapleton ............... C12N 15/00 436/515 |
| 5,503,980 A | 4/1996 | Cantor |
| 5,559,032 A | 9/1996 | Pomeroy et al. |
| 5,641,658 A | 6/1997 | Adams et al. |
| 5,658,751 A | 8/1997 | Yue et al. |
| 5,716,825 A | 2/1998 | Hancock et al. |
| 5,750,341 A | 5/1998 | Macevicz |
| 5,763,175 A | 6/1998 | Brenner |
| 6,013,440 A | 1/2000 | Lipshutz et al. |
| 6,083,761 A | 7/2000 | Kedar et al. |
| 6,136,592 A | 10/2000 | Leighton |
| 6,143,496 A | 11/2000 | Brown et al. |
| 6,157,432 A | 12/2000 | Helbing |
| 6,165,714 A | 12/2000 | Lane et al. |
| 6,210,894 B1 | 4/2001 | Brennan |
| 6,214,587 B1 | 4/2001 | Dattagupta et al. |
| 6,221,654 B1 | 4/2001 | Quake |
| 6,266,459 B1 | 7/2001 | Walt et al. |
| 6,274,320 B1 | 8/2001 | Rothberg et al. |
| 6,291,180 B1 | 9/2001 | Chu |
| 6,309,824 B1 | 10/2001 | Drmanac |
| 6,337,472 B1 | 1/2002 | Garner et al. |
| 6,344,316 B1 | 2/2002 | Lockhart et al. |
| 6,348,990 B1 | 2/2002 | Igasaki et al. |
| 6,355,431 B1 | 3/2002 | Chee et al. |
| 6,401,267 B1 | 6/2002 | Drmanac |
| 6,404,907 B1 | 6/2002 | Gilchrist et al. |
| 6,426,215 B1 * | 7/2002 | Sandell ............... B01L 3/50853 435/305.3 |
| 6,432,360 B1 | 8/2002 | Church |
| 6,485,982 B1 | 11/2002 | Charlton |
| 6,544,732 B1 | 4/2003 | Chee et al. |
| 6,544,790 B1 | 4/2003 | Sabatini |
| 6,565,727 B1 | 5/2003 | Shenderov |
| 6,620,584 B1 | 9/2003 | Chee et al. |
| 6,632,641 B1 | 10/2003 | Brennan et al. |
| 6,673,620 B1 | 1/2004 | Loeffler et al. |
| 6,770,441 B2 | 8/2004 | Dickinson et al. |
| 6,773,566 B2 | 8/2004 | Shenderov |
| 6,787,308 B2 | 9/2004 | Balasubramanian et al. |
| 6,812,005 B2 | 11/2004 | Fan et al. |
| 6,911,132 B2 | 6/2005 | Pamula |
| 6,911,345 B2 | 6/2005 | Quake |
| 6,913,921 B2 | 7/2005 | Fischer |
| 6,969,488 B2 | 11/2005 | Bridgham |
| 6,977,033 B2 | 12/2005 | Becker |
| 7,001,792 B2 | 2/2006 | Sauer et al. |
| 7,052,244 B2 | 5/2006 | Fouillet |
| 7,098,041 B2 | 8/2006 | Kaylor et al. |
| 7,163,612 B2 | 1/2007 | Sterling |
| 7,166,431 B2 | 1/2007 | Chee et al. |
| 7,223,371 B2 | 5/2007 | Hayenga et al. |
| 7,244,559 B2 | 7/2007 | Rothberg |
| 7,255,994 B2 | 8/2007 | Lao |
| 7,264,929 B2 | 9/2007 | Rothberg |
| 7,328,979 B2 | 2/2008 | Decre |
| 7,393,665 B2 | 7/2008 | Brenner |
| 7,456,012 B2 | 11/2008 | Ryttsen et al. |
| 7,462,449 B2 | 12/2008 | Quake |
| 7,501,245 B2 | 3/2009 | Quake |
| 7,547,380 B2 | 6/2009 | Velev |
| 7,561,336 B2 | 7/2009 | Osaka et al. |
| 7,595,883 B1 | 9/2009 | El Gamal |
| 7,601,492 B2 | 10/2009 | Fu et al. |
| 7,641,779 B2 | 1/2010 | Becker |
| 7,709,198 B2 | 5/2010 | Luo et al. |
| 7,785,869 B2 | 8/2010 | Belgrader et al. |
| 7,858,321 B2 | 12/2010 | Glezer |
| 8,206,917 B2 | 6/2012 | Chee et al. |
| 8,278,034 B2 | 10/2012 | Muraca |
| 8,330,087 B2 | 12/2012 | Domenicali |
| 8,460,865 B2 | 6/2013 | Chee et al. |
| 8,604,182 B2 | 12/2013 | Luo et al. |
| 8,637,242 B2 | 1/2014 | Shen |
| 8,778,849 B2 | 7/2014 | Bowen |
| 8,900,529 B2 | 12/2014 | Shaikh et al. |
| 8,951,726 B2 | 2/2015 | Luo et al. |
| 8,951,781 B2 | 2/2015 | Reed et al. |
| 9,201,063 B2 | 12/2015 | Sood et al. |
| 9,371,598 B2 | 6/2016 | Chee |
| 9,416,409 B2 | 8/2016 | Hayden |
| 9,557,330 B2 | 1/2017 | Siciliano et al. |
| 9,582,877 B2 | 2/2017 | Fu et al. |
| 9,593,365 B2 | 3/2017 | Frisen et al. |
| 9,727,810 B2 | 8/2017 | Fodor et al. |
| 9,783,841 B2 | 10/2017 | Nolan et al. |
| 9,868,979 B2 | 1/2018 | Chee et al. |
| 9,975,122 B2 | 5/2018 | Masquelier et al. |
| 10,002,316 B2 | 6/2018 | Fodor et al. |
| 10,032,064 B2 | 7/2018 | Hoyt |
| 10,041,949 B2 | 8/2018 | Bendall et al. |
| 10,053,723 B2 | 8/2018 | Hindson et al. |
| 10,059,990 B2 | 8/2018 | Boyden et al. |
| 10,071,377 B2 | 9/2018 | Bharadwaj et al. |
| 10,246,700 B2 | 4/2019 | Dunaway et al. |
| 10,266,888 B2 | 4/2019 | Daugharthy et al. |
| 10,428,326 B2 | 10/2019 | Belhocine et al. |
| 10,495,554 B2 | 12/2019 | Deisseroth et al. |
| RE50,065 E | 7/2024 | Frisen et al. |
| 12,024,741 B2 | 7/2024 | Tentori et al. |
| 12,031,177 B1 | 7/2024 | Tentori et al. |
| 2002/0022261 A1 | 2/2002 | Anderson et al. |
| 2002/0040275 A1 | 4/2002 | Cravatt et al. |
| 2002/0045272 A1 | 4/2002 | McDevitt et al. |
| 2002/0150909 A1 | 10/2002 | Stuelpnagel et al. |
| 2002/0164611 A1 | 11/2002 | Bamdad |
| 2003/0113713 A1 | 6/2003 | Glezer |
| 2003/0175844 A1 | 9/2003 | Nadler et al. |
| 2003/0175947 A1 | 9/2003 | Liu et al. |
| 2003/0190744 A1 | 10/2003 | McGarry et al. |
| 2003/0205632 A1 | 11/2003 | Kim et al. |
| 2003/0215936 A1 | 11/2003 | Kallioniemi et al. |
| 2004/0050699 A1 | 3/2004 | Goncalves |
| 2004/0067492 A1 | 4/2004 | Peng et al. |
| 2004/0082058 A1 | 4/2004 | Schleifer et al. |
| 2004/0082059 A1 | 4/2004 | Webb et al. |
| 2004/0112442 A1 | 6/2004 | Maerkl et al. |
| 2004/0121456 A1 | 6/2004 | Fischer |
| 2004/0219588 A1 | 11/2004 | Furuta |
| 2004/0248287 A1 | 12/2004 | Hu et al. |
| 2005/0095627 A1 | 5/2005 | Kolman et al. |
| 2005/0106617 A1 | 5/2005 | Besemer et al. |
| 2005/0116161 A1 | 6/2005 | Hafeman et al. |
| 2005/0179746 A1 | 8/2005 | Roux et al. |
| 2005/0226780 A1 | 10/2005 | Sandell et al. |
| 2005/0239192 A1 | 10/2005 | Nasarabadi et al. |
| 2006/0039823 A1 | 2/2006 | Yamakawa et al. |
| 2006/0063160 A1 | 3/2006 | West et al. |
| 2006/0134669 A1 | 6/2006 | Casasanta |
| 2006/0164490 A1 | 7/2006 | Kim et al. |
| 2006/0194331 A1 | 8/2006 | Pamula et al. |
| 2007/0023292 A1 | 2/2007 | Kim et al. |
| 2007/0036511 A1 | 2/2007 | Lundquist et al. |
| 2007/0099208 A1 | 5/2007 | Drmanac et al. |
| 2007/0116612 A1 | 5/2007 | Williamson, IV |
| 2007/0128071 A1 * | 6/2007 | Shea ................... B01J 19/0046 422/400 |
| 2007/0166725 A1 | 7/2007 | McBride et al. |
| 2007/0184456 A1 | 8/2007 | Chee et al. |
| 2007/0215466 A1 | 9/2007 | Okada |
| 2007/0243634 A1 | 10/2007 | Pamula et al. |
| 2007/0264656 A1 | 11/2007 | Kawamura |
| 2008/0043235 A1 * | 2/2008 | Oldham ............. G01N 21/6456 356/344 |
| 2008/0145616 A1 | 6/2008 | Gharib et al. |
| 2008/0218838 A1 | 9/2008 | Rey-Mermet |
| 2009/0005252 A1 | 1/2009 | Drmanac et al. |
| 2009/0011943 A1 | 1/2009 | Drmanac et al. |
| 2009/0018024 A1 | 1/2009 | Church et al. |
| 2009/0023148 A1 | 1/2009 | Moyle et al. |

(56) References Cited

U.S. PATENT DOCUMENTS

| | | |
|---|---|---|
| 2009/0068667 A1 | 3/2009 | Meisner et al. |
| 2009/0169089 A1 | 7/2009 | Hunt et al. |
| 2009/0192044 A1 | 7/2009 | Fouillet |
| 2009/0197326 A1 | 8/2009 | El Gamal et al. |
| 2009/0226911 A1* | 9/2009 | Mauk ............... G01N 31/20 435/6.12 |
| 2009/0239232 A1 | 9/2009 | Kurn |
| 2009/0253163 A1 | 10/2009 | Xie et al. |
| 2009/0253582 A1 | 10/2009 | Pena et al. |
| 2009/0321262 A1 | 12/2009 | Adachi et al. |
| 2010/0009871 A1 | 1/2010 | Reed et al. |
| 2010/0031757 A1 | 2/2010 | Hoyer |
| 2010/0035249 A1 | 2/2010 | Hayashizaki et al. |
| 2010/0096266 A1 | 4/2010 | Kim et al. |
| 2010/0111768 A1 | 5/2010 | Banerjee et al. |
| 2010/0126862 A1 | 5/2010 | Sabin et al. |
| 2010/0151511 A1 | 6/2010 | Greenizen et al. |
| 2010/0210475 A1 | 8/2010 | Lee et al. |
| 2010/0267590 A1 | 10/2010 | Grudzien et al. |
| 2010/0273219 A1 | 10/2010 | May et al. |
| 2010/0273679 A1 | 10/2010 | Cuppoletti et al. |
| 2010/0282617 A1 | 11/2010 | Rothberg et al. |
| 2011/0028685 A1 | 2/2011 | Purkayastha et al. |
| 2011/0048951 A1 | 3/2011 | Wu |
| 2011/0177518 A1 | 7/2011 | Kartalov et al. |
| 2011/0244448 A1 | 10/2011 | Shirai et al. |
| 2012/0160683 A1 | 6/2012 | Ye et al. |
| 2012/0177543 A1 | 7/2012 | Battrell |
| 2012/0195810 A1 | 8/2012 | Cohen et al. |
| 2012/0270305 A1 | 10/2012 | Reed et al. |
| 2012/0279954 A1* | 11/2012 | Ceremony ............... B01L 7/52 219/243 |
| 2012/0316086 A1* | 12/2012 | Lin ............... G01N 27/447 506/26 |
| 2013/0052331 A1 | 2/2013 | Kram et al. |
| 2013/0053273 A1 | 2/2013 | Juncker et al. |
| 2013/0065788 A1 | 3/2013 | Glezer et al. |
| 2013/0096033 A1 | 4/2013 | Routenberg |
| 2013/0146459 A1 | 6/2013 | Bazant et al. |
| 2013/0203100 A1 | 8/2013 | Otter et al. |
| 2013/0252847 A1* | 9/2013 | McKenna ........ G01N 33/54366 506/13 |
| 2013/0260372 A1 | 10/2013 | Buermann et al. |
| 2013/0296174 A1 | 11/2013 | Peumans |
| 2014/0011289 A1* | 1/2014 | Smith ............... B01L 7/00 422/551 |
| 2014/0011707 A1 | 1/2014 | Ye et al. |
| 2014/0066318 A1 | 3/2014 | Frisen et al. |
| 2014/0155295 A1 | 6/2014 | Hindson et al. |
| 2014/0323330 A1 | 10/2014 | Bergo |
| 2015/0148239 A1 | 5/2015 | Peter et al. |
| 2015/0219618 A1 | 8/2015 | Krishnan et al. |
| 2015/0298091 A1 | 10/2015 | Weitz et al. |
| 2016/0033496 A1 | 2/2016 | Chou et al. |
| 2016/0289669 A1 | 10/2016 | Fan et al. |
| 2016/0299165 A1 | 10/2016 | Zhou |
| 2017/0016053 A1 | 1/2017 | Beechem et al. |
| 2017/0266667 A1* | 9/2017 | Mortillaro ............... B01L 7/52 |
| 2017/0349940 A1 | 12/2017 | Morin et al. |
| 2018/0052082 A1 | 2/2018 | Groll et al. |
| 2018/0074039 A1 | 3/2018 | Soper et al. |
| 2018/0080876 A1 | 3/2018 | Rockel et al. |
| 2018/0095067 A1 | 4/2018 | Huff et al. |
| 2018/0104694 A1 | 4/2018 | Huff et al. |
| 2018/0104964 A1 | 4/2018 | Uemura et al. |
| 2018/0127817 A1 | 5/2018 | Borchert et al. |
| 2018/0217094 A1 | 8/2018 | Herr et al. |
| 2018/0245142 A1 | 8/2018 | So et al. |
| 2018/0251833 A1 | 9/2018 | Daugharthy et al. |
| 2018/0257075 A1 | 9/2018 | Yellen et al. |
| 2018/0305681 A1 | 10/2018 | Jovanovich et al. |
| 2019/0099754 A1 | 4/2019 | Dupouy et al. |
| 2019/0113532 A1* | 4/2019 | Tan ............... G01N 33/536 |
| 2019/0126280 A1 | 5/2019 | Gach et al. |
| 2019/0155835 A1 | 5/2019 | Daugharthy et al. |
| 2019/0201891 A1* | 7/2019 | Pallas ............... C12Q 1/686 |
| 2019/0218276 A1 | 7/2019 | Regev et al. |
| 2019/0262831 A1 | 8/2019 | West et al. |
| 2020/0049599 A1 | 2/2020 | Alexander et al. |
| 2020/0277663 A1 | 9/2020 | Ramachandran Iyer et al. |
| 2020/0277664 A1 | 9/2020 | Frenz |
| 2020/0298241 A1 | 9/2020 | Kabaha et al. |
| 2020/0325531 A1 | 10/2020 | Chee |
| 2020/0363408 A1 | 11/2020 | Chou et al. |
| 2020/0393343 A1 | 12/2020 | Kennedy-Darling et al. |
| 2021/0095331 A1 | 4/2021 | Fan et al. |
| 2021/0130881 A1 | 5/2021 | Cox |
| 2024/0200121 A1 | 6/2024 | Boutet |
| 2024/0209425 A1 | 6/2024 | Yin et al. |
| 2024/0218427 A1 | 7/2024 | Sukovich et al. |
| 2024/0218432 A1 | 7/2024 | Mielinis |
| 2024/0219701 A1 | 7/2024 | Tentori et al. |

FOREIGN PATENT DOCUMENTS

| | | | |
|---|---|---|---|
| CN | 1425133 | 6/2003 | |
| CN | 1981188 | 6/2007 | |
| CN | 202548048 | 11/2012 | |
| CN | 102851369 | 1/2013 | |
| CN | 104513785 | 4/2015 | |
| EP | 0961110 A2 | 12/1999 | |
| EP | 0961110 A3 | 12/1999 | |
| EP | 0901631 B1 | 8/2004 | |
| EP | 1 782 737 A1 | 5/2007 | |
| EP | 1878502 A1 | 1/2008 | |
| EP | 1923471 A1 | 5/2008 | |
| EP | 1923471 B1 | 5/2008 | |
| EP | 2881465 | 6/2015 | |
| EP | 3013983 A1 | 5/2016 | |
| EP | 3013984 A1 | 5/2016 | |
| EP | 2350648 B1 | 3/2017 | |
| EP | 2350648 B8 | 3/2017 | |
| EP | 1846164 B1 * | 5/2018 | ......... A61B 10/0051 |
| WO | WO-89/010977 A1 | 11/1989 | |
| WO | WO-95/025116 A1 | 9/1995 | |
| WO | WO-95/035505 A1 | 12/1995 | |
| WO | WO 1999/063385 | 12/1999 | |
| WO | WO 2002/040874 | 5/2002 | |
| WO | WO-02/077283 A1 | 10/2002 | |
| WO | WO-03/002979 A2 | 1/2003 | |
| WO | WO-03/002979 A3 | 1/2003 | |
| WO | WO 2003/106973 | 12/2003 | |
| WO | WO 2004/028955 | 4/2004 | |
| WO | WO-2004/108268 A1 | 12/2004 | |
| WO | WO-2005/007814 A2 | 1/2005 | |
| WO | WO-2005/007814 A3 | 1/2005 | |
| WO | WO 2006/056861 | 6/2006 | |
| WO | WO-2007/076726 A1 | 7/2007 | |
| WO | WO 2007/120241 | 10/2007 | |
| WO | WO 2007/123744 | 11/2007 | |
| WO | 2008157801 A2 | 12/2008 | |
| WO | WO-2010/126614 A2 | 11/2010 | |
| WO | WO-2010/126614 A3 | 11/2010 | |
| WO | WO 2011/094669 | 8/2011 | |
| WO | WO-2011/102903 A1 | 8/2011 | |
| WO | WO 2011/127099 | 10/2011 | |
| WO | WO 2012/058096 | 5/2012 | |
| WO | WO 2012/140224 | 10/2012 | |
| WO | WO 2012/168003 | 12/2012 | |
| WO | WO 2014/060483 | 4/2014 | |
| WO | WO 2014/128129 | 8/2014 | |
| WO | WO-2014/142841 A1 | 9/2014 | |
| WO | WO 2014/163886 | 10/2014 | |
| WO | WO-2014/210223 A1 | 12/2014 | |
| WO | WO 2014/210225 | 12/2014 | |
| WO | WO 2014/210233 | 12/2014 | |
| WO | WO 2015/161173 | 10/2015 | |
| WO | WO 2016/007839 | 1/2016 | |
| WO | WO 2016/057552 | 4/2016 | |
| WO | WO-2016/126882 A1 | 8/2016 | |
| WO | WO-2016/138496 A1 | 9/2016 | |
| WO | WO-2016/138500 A1 | 9/2016 | |
| WO | WO-2016/162309 A1 | 10/2016 | |

(56) References Cited

FOREIGN PATENT DOCUMENTS

| WO | WO 2016/166128 | 10/2016 |
|---|---|---|
| WO | WO-2016/168825 A1 | 10/2016 |
| WO | WO 2016/172362 | 10/2016 |
| WO | WO-2017/019456 A2 | 2/2017 |
| WO | WO-2017/019456 A3 | 2/2017 |
| WO | WO 2017/027367 | 2/2017 |
| WO | WO 2017/027368 | 2/2017 |
| WO | WO-2017/048871 A1 | 3/2017 |
| WO | WO-2017/112957 A1 | 6/2017 |
| WO | WO 2017/144338 | 8/2017 |
| WO | WO 2017/147483 | 8/2017 |
| WO | WO 2017/222453 | 12/2017 |
| WO | WO 2018/022809 | 2/2018 |
| WO | WO 2018/045181 | 3/2018 |
| WO | WO 2018/045186 | 3/2018 |
| WO | WO 2018/057999 | 3/2018 |
| WO | WO-2018/075436 A1 | 4/2018 |
| WO | WO-2018/091676 A1 | 5/2018 |
| WO | WO 2018/107054 | 6/2018 |
| WO | WO 2018/136856 | 7/2018 |
| WO | 2018148471 A2 | 8/2018 |
| WO | WO-2018/144582 A1 | 8/2018 |
| WO | 2019012005 A1 | 1/2019 |
| WO | WO 2019/068880 | 4/2019 |
| WO | WO 2019/075091 | 4/2019 |
| WO | WO 2019/104337 | 5/2019 |
| WO | WO 2019/113457 | 6/2019 |
| WO | WO-2019/140334 A1 | 7/2019 |
| WO | 2020047004 A2 | 3/2020 |
| WO | WO 2020/123320 A2 | 6/2020 |
| WO | WO 2020/123320 A3 | 6/2020 |
| WO | WO 2021/016379 | 1/2021 |
| WO | WO 2021/067246 | 4/2021 |
| WO | WO 2021/116715 | 6/2021 |
| WO | WO 2022/051152 | 3/2022 |
| WO | WO 2023/122033 | 6/2023 |
| WO | WO 2024/137826 | 6/2024 |
| WO | WO 2024/145224 | 7/2024 |
| WO | WO 2024/145441 | 7/2024 |
| WO | WO 2024/145445 | 7/2024 |
| WO | WO 2024/145491 | 7/2024 |

OTHER PUBLICATIONS

Anonymous (Dec. 13, 2021) "Visium Spatial Gene Expression Imaging Guidelines", 10xGenomics Inc., pp. 1-11.

Asp et al. (May 4, 2020) "Spatially Resolved Transcriptomes—Next Generation Tools for Tissue Exploration", Bioessays, 42(10):1900221(16 pages).

Cardona et al. (Sep. 8, 2011) "TrakEM2 0.9a User Manual", TrakEM2, 38 pages.

Navarro et al. (Mar. 15, 2019) "ST Viewer: A Tool for Analysis and Visualization of Spatial Transcriptomics Datasets", Bioinformatics, 35(6):1058-1060.

Wilbrey-Clark et al. (Apr. 27, 2020) "Cell Atlas Technologies and Insights Into Tissue Architecture", The Biochemical Journal, 477(8):1427-1442.

Wong et al. (Jun. 1, 2018) "ST Spot Detector: A Web-Based Application for Automatic Spot and Tissue Detection for Spatial Transcriptomics Image Datasets", Bioinformatics, 34(11):1966-1968.

U.S. Appl. No. 61/839,313, filed Jun. 25, 2013, Chee et al.

U.S. Appl. No. 61/839,320, filed Jun. 25, 2013, Chee et al.

Affymetrix, "GeneChip Human Genome Arrays, GeneChip® Human Genome U133 Plus 2.0 Array," located at<www.affymetrix.com/support/technical/datasheets/hgu133_datasheet.pdf> retrieved on Feb. 26, 2003, 4 pages.

Affymetrix, Data Sheet, "GeneChip® Human Genome U95 Set," located at <www.affymetrix.com,> retrieved on Oct. 2, 2002, 2 pages.

Armani, M. et al. (Dec. 21, 2009). "2D-PCR: a method of mapping DNA in tissue sections," Lab on a Chip 9(24):3526-3534.

Beechem, J.M. (2020). "High-Plex Spatially Resolved RNA and Protein Detection Using Digital Spatial Profiling: A Technology Designed for Immuno-oncology Biomarker Discovery and Translational Research," Chapter 25 in *Biomarkers for Immunotherapy of Cancer: Methods and Protocols, Methods in Molecular Biology*, pp. 563-583.

Birney, E. et al, (Jun. 14, 2007). "Identification and analysis of functional elements in 1% of the human genome by the ENCODE pilot project," *Nature* 447(7146):799-816.

Blokzijl, A. et al. (Sep. 2010). "Profiling protein expression and interactions: proximity ligation as a tool for personalized medicine," *J Intern. Med*. 268(3):232-245.

Blow, N. (Aug. 23, 2007). "Tissue preparation: Tissue issues," *Nature* 448(23), 959-962.

Brenner, S. et al. (Jun. 2000). "Gene expression analysis by massively parallel signature sequencing (MPSS) on microbead arrays," *Nat. Biotech*. 18(6):630-634.

Burgess, D.J. (Jul. 15, 2016). "Gene expression: A space for transcriptomics," *Nature Reviews Genetics*, 1 page.

Burgess, D.J. (Apr. 13, 2018). "Transcriptomics: Finding structure in gene expression," *Nature Reviews Genetics* 19(5):249.

Burton, M.P. et al. (Jan. 1998). "Coverslip mounted-immersion cycled in situ RT-PCR for the localization of mRNA in tissue sections," *Biotechniques* 24(1):92-100.

Chandra, H. et al. (Feb. 2010). "Cell-free synthesis-based protein microarrays and their applications," *Proteomics* 5(6):717-730.

Constantine et al. (1998). "Use of genechip high-density oligonucleotide arrays for gene expression monitoring," Life Sceience News, Amersham Life Science; 11-14.

Crosetto, N. et al. (Jan. 2015, e-published Dec. 2, 2014). "Spatially resolved transcriptomics and beyond," *Nature Review Genetics* 16(1):57-66.

Eguiluz, C. et al. (2006, e-published Jun. 19, 2006). "Multitissue array review: a chronological description of tissue array techniques, applications and procedures," *Pathology Research and Practice* 202(8):561-568.

Fodor, S.P. et al. (Feb. 15, 1991). "Light-directed, spatially addressable parallel chemical synthesis," *Science* 251(4995):767-773.

Gene Arrays Services, BeadArray Technology, available on or before Feb. 14, 2015, located at <http://genearrays.com/services/microarrays/illumina/beadarray-technology> [retrieved on Jan. 30, 2020], 1 page.

Gnanapragasam, V.J. (Jan. 2010, e-published Jun. 10, 2009). "Unlocking the molecular archive: the emerging use of formalin-fixed paraffin-embedded tissue for biomarker research in urological cancer," *BJU International* 105(2):274-278.

Gunderson, K.L. et al. (May 2004, e-published Apr. 12, 2004). "Decoding randomly ordered DNA arrays," *Genome Research* 14(5):870-877.

He, M. et al. (Feb. 2008, e-published Jan. 18, 2008). "In situ synthesis of protein arrays," *Current Opinion in Biotechnology* 19(1):4-9.

Jemt, A. et al. (Nov. 16, 2016). "An automated approach to prepare tissue-derived spatially barcoded RNA-sequencing libraries," *Scientific Reports* 6:37137, 10 pages.

Lage, J.M. et al. (Feb. 2003). "Whole genome analysis of genetic alterations in small DNA samples using hyperbranched strand displacement amplification and array-CGH," Genome Research 13(2):294-307.

Miller, M.B. et al. (Oct. 2009). "Basic concepts of microarrays and potential applications in clinical microbiology," *Clinical Microbiology Reviews*, 22(4):611-633.

Pettersson, E. et al. (Feb. 2009, e-published Nov. 21, 2008). "Generations of sequencing technologies," *Genomics* 93(2):105-111.

Schena, M. et al. (Oct. 20, 1995). "Quantitative monitoring of gene expression patterns with a complementary DNA microarray," *Science* 270(5235):467-470.

Stahl, P.L. et al. (Jul. 1, 2016). "Visualization and analysis of gene expression in tissue sections by spatial transcriptomics," *Science* 353(6294):78-82.

(56) References Cited

OTHER PUBLICATIONS

Strell, C. et al. (Apr. 2019, e-published Mar. 31, 2018). "Placing RNA in context and space—methods for spatially resolved transcriptomics," *The FEBS Journal* 286(8):1468-1481.
Final Office Action mailed on Jan. 31, 2022, for U.S. Appl. No. 17/172,926, filed Feb. 10, 2021, 33 pages.
Final Office Action mailed on Sep. 14, 2022, for U.S. Appl. No. 17/172,926, filed Feb. 10, 2021, 30 pages.
Final Office Action mailed on Jan. 26, 2023, for U.S. Appl. No. 17/172,926, filed Feb. 10, 2021, 24 pages.
Final Office Action mailed on Sep. 20, 2022, for U.S. Appl. No. 17/665,169, filed Feb. 4, 2022, 8 pages.
Forster, S.C. et al. (Feb. 2019, e-published Feb. 4, 2019). "A human gut bacterial genome and culture collection for improved metagenomic analyses," *Nature Biotechnology* 37(2):186-192.
Gabbatiss, J. et al. (Apr. 24, 2018). "New form of DNA discovered inside living human cells," *The Independent*, 2 pages.
"Human Genome" Wikipedia .com located at < https://en.wikipedia.org/wiki/Human_genome#:~:text=The%20human%20genome%20is%20a,genome%20and%20the%20mitochondrial%20genome> last accessed Feb. 7, 2024, 33 pages.
International Preliminary Report on Patentability mailed on Jun. 8, 2021, for PCT Application No. PCT/US2019/065100, filed Dec. 6, 2019, 13 pages.
International Search Report mailed on Jun. 23, 2020, for PCT Application No. PCT/US2019/065100, filed Dec. 6, 2019, 8 pages.
International Preliminary Report on Patentability mailed on Sep. 28, 2021, for PCT Application No. PCT/US2020/029843, filed Apr. 24, 2020, 14 pages.
International Search Report mailed on Oct. 7, 2020, for PCT Application No. PCT/US2020/029843, filed Apr. 24, 2020, 6 pages.
Liu, H. et al. (Dec. 15, 2010, e-published Jul. 30, 2010). "An integrated and sensitive detection platform for biosensing application based on Fe@Au magnetic nanoparticles as bead array carries," *Biosensors and Bioelectronics* 26(4):1442-1448.
Non-Final Office Action mailed on May 10, 2021, for U.S. Appl. No. 17/172,926, filed Feb. 10, 2021, 33 pages.
Non-Final Office Action mailed on May 12, 2022, for U.S. Appl. No. 17/665,169, filed Feb. 4, 2022, 7 pages.
Non-Final Office Action mailed on Aug. 3, 2023, for U.S. Appl. No. 17/665,169, filed Feb. 4, 2022, 6 pages.
Non-Final Office Action mailed on Nov. 27, 2023, for U.S. Appl. No. 17/665,169, filed Feb. 4, 2022, 8 pages.
Non-Final Office Action mailed on May 22, 2023, for U.S. Appl. No. 18/049,094, filed Oct. 24, 2022, 32 pages.
Sah, R. et al. (Mar. 12, 2020). "Complete Genome Sequence of a 2019 Novel Coronavirus (SARS-CoV-2) Strain Isolated in Nepal," *Microbiology Resource Announcements* 9(11):e00169-20.
Sumitomo, K. et al. (Jan. 15, 2012, e-published Nov. 15, 2011). "Ca2+ ion transport through channels formed by α-hemolysin analyzed using a microwell array on a Si substrate," *Biosensors and Bioelectronics* 31(1):445-450.
Wu, L. et al. (Jun. 18, 2010). "Detection DNA point mutation with rolling-circle amplification chip," Bioinformatics and Biomedical Engineering (ICBBE), 2010 4th International Conference, IEEE, Piscataway, NJ, USA pp. 1-4.
Zeberg, H. et al. (Nov. 2020, e-published Sep. 30, 2020). "The major genetic risk factor for severe COVID-19 is inherited from Neanderthals," *Nature* 587(7835):610-612.
Andor.com [online], "Discover new ways of seeing," Next Generation Digital Illumination, Mosaic 3, 2020, 11 pages.
Blair et al., "Microarray temperature optimization using hybridization kinetics," Methods Mol Biol., 2009, 529:171-96.
Borm et al., "Scalable in situ single-cell profiling by electrophoretic capture of mRNA," bioRxiv, Jan. 2022, 32 pages.
Calvert, "Materials science. Printing cells," Science, Oct. 2007, 318(5848):208-209.
Carter et al., "Stabilization of an optical microscope to 0.1 nm in three dimensions," Applied Optics, 2007, 46:421-427.
Chen et al., "DNA hybridization detection in a microfluidic Channel using two fluorescently labelled nucleic acid probes," Biosensors and Bioelectronics, 2008, 23(12):1878-1882.
Chen et al., "RNA imaging. Spatially resolved, highly multiplexed RNA profiling in single cells," Science, Apr. 2015, 348(6233):aaa6090, 21 pages.
Cockroft et al., "A single-molecule nanopore device detects DNA polymerase activity with single-nucleotide resolution," J Am Chem Soc., Jan. 2008, 130(3):818-20.
Deamer et al., "Characterization of nucleic acids by Nanopore analysis," Acc Chem Res., Oct. 2002, 35(10):817-25.
Dhindsa et al., "Virtual Electrowetting Channels: Electronic Liquid Transport with Continuous Channel Functionality," Lab Chip, 2010, 10:832-836.
Eastburn, "Microfluidic droplet enrichment for targeted sequencing," Nucleic Acids Research, 2015, 43(13):1-8.
Fahy et al., "Design and synthesis of polyacrylamide-based oligonucleotide supports for use in nucleic acid diagnostics," Nucleic Acids Res., Apr. 1993, 21(8):1819-26.
Fluidigm, "Hyperion Imaging System: Visualize a new path forward," Feb. 2018, retrieved from URL <https://www.fluidigm.com/binaries/content/documents/fluidigm/search/hippo%3Aresultset/hyperion-imaging-system-br-400326/fluidigm%3Afile>, 27 pages.
Fluidigm, "Immuno-Oncology Research with the Hyperion Imaging System: A high-parameter imaging solution at subcellular resolution to characterize the immune repertoire in the tumor microenvironment," Apr. 2018, retrieved from URL <https://www.fluidigm.com/binaries/content/documents/fluidigm/search/hippo%3Aresultset/application-note-immuno-oncology-research-with-the-hyperion%E2%84%A2-imaging-system/fluidigm%3Afile>, 6 pages.
Fluidigm, "Immuno-Oncology Research with the Hyperion Imaging System: A high-parameter imaging solution at subcellular resolution to characterize the immune repertoire in the tumor microenvironment," Aug. 2018, retrieved from URL <https://www.fluidigm.com/binaries/content/documents/fluidigm/marketing/immuno-oncology-research-with-the-hyperion-imaging-system-appnote-400332/immuno-oncology-research-with-the-hyperion-imaging-system-appnote-400332/fluidigm%3Afile>, 6 pages.
Fluidigm, "Maxpar Antibodies for Imaging Mass Cytometry," Mar. 2018, retrieved from URL <https://www.fluidigm.com/binaries/content/documents/fluidigm/search/hippo%3Aresultset/hyperion-antibodies-for-imaging-mass-cytometry-br-101-7115/fluidigm%3Afile>, 2 pages.
Forcucci et al., "All-plastic miniature fluorescence microscope for point-of-care readout of bead-based bioassays.," J. Biomed Opt., 2015, 20(10):105010, 15 pages.
Gamper et al., "Gene expression profile of bladder tissue of patients with ulcerative interstitial cystitis," BMC Genomics, Apr. 28, 2009, 10(199):1-17.
Gao et al., "Q&A: Expansion microscopy," BMC Biology, 15:50, 9 pages, 2017.
Gupta et al., "Single-cell isoform RNA sequencing characterizes isoforms in thousands of cerebellar cells," Nature Biotechnol., Oct. 2018, 36:1197-1202.
Hattersley et al., "Development of a microfluidic device for the maintenance and interrogation of viable tissue biopsies," Lab Chip., Nov. 2008, 8(11):1842-6.
Hoyer et al., "Electrostatic spraying: a novel technique for preparation of polymer coatings on electrodes," Anal Chem, Nov. 1996, 68(21):3840-4.
Kim et al., "Replication of DNA Microarrays Prepared by In Situ Oligonucleotide Polymerization and Mechanical Transfer," Anal Chem., 2007, 79:7267-7274.
Kim, "Development of Microdevices for Applications to Bioanalysis," Dissertation for the degree of Doctor of Philosophy, University of Texas at Austin, Aug. 2007, 176 pages.
Lamture et al., "Direct detection of nucleic acid hybridization on the surface of a charge coupled device," Nucleic Acid Res., Jun. 1994, 22(11):2121-5.
Lee et al., "Fluorescent in situ sequencing (FISSEQ) of RNA for gene expression profiling in intact cells and tissues," Nature Protocols, 2015, 10(3):442-458.

(56) References Cited

OTHER PUBLICATIONS

Levene et al., "Zero-Mode Waveguides for Single-Molecule Analysis at High Concentrations," Science, 2003, 299:682-686.

Li et al., "DNA molecules and configurations in a solid-state nanopore microscope," Nat Mater., Sep. 2003, 2(9):611-5.

Lin et al., "Microfluidic cell trap array for controlled positioning of single cells on adhesive micropatterns," Lab Chip, Feb. 2013, 13(4):714-721.

Lu et al., "A microfluidic electroporation device for cell lysis," Lab Chip., Jan. 2005, 5(1):23-29.

Lundquist et al., "Parallel confocal detection of single molecules in real time," Opt. Lett., 2008, 33:1026-1028.

Rodriques et al., "Slide-seq: A scalable technology for measuring genome-wide expression at high spatial resolution," Science, 2019, 363(6434):1463-1467.

Rountenberg et al., "Microfluidic probe: a new tool for integrating microfluidic environments and electronic wafer-orobina," Lab Chip, Oct. 2009, 10: 123-127.

Soni and Meller, "Progress toward ultrafast DNA sequencing using solid-state nanopores," Clin Chem., 2007, 53:1996-2001.

Stahl et al., "Visualization and analysis of gene expression in tissue sections by spatial transcriptomics," Supplementary Materials, Science, Jul. 2016, 353(6294):78-82, 41 pages.

Taylor et al., "Microfluidic local perfusion chambers for the visualization and manipulation of synapses," Neuron., Apr. 2010, 66(1):57-68, 25 pages.

Thomas et al., "A chamber for the perfusion of in vitro tissue with multiple solutions," J. Neurophysiol., Jul. 2013, 110:269-277.

Toy et al., "A Simple Plastic Perfusion Chamber for Continuous Maintenance and Cinematography of Tissue Cultures," Experimental Cell Research, 1958, 14:97-103.

Trejo et al., "Extraction-free whole transcriptome gene expression analysis of FFPE sections and histology-directed subareas of tissue," PLoS ONE, Feb. 2019, 14(2):e0212031, 22 pages.

Valley et al., "Optoelectronic tweezers as a tool for parallel single-cell manipulation and stimulation," IEEE Trans Biomed Circuits Syst., Dec. 2009, 3(6):424-31.

Wang et al., "Concentration gradient generation methods based on microfluidic systems," RSC Adv., 2017, 7:29966-29984.

Wheeler et al., "Microfluidic device for single-cell analysis," Analytical Chemistry, Jul. 2003, 75(14):3581-3586.

Yoda et al., "Site-specific gene expression analysis using an automated tissue micro-dissection punching system," Sci Rep., Jun. 2017, 7(1):4325, 11 pages.

\* cited by examiner

IMAGING SYSTEM HARDWARE

CROSS-REFERENCE TO RELATED APPLICATIONS

This application claims priority to Provisional Patent Application No. 62/931,779, filed Nov. 6, 2019.

The contents of these applications are incorporated by reference in their entireties.

BACKGROUND

Cells within a tissue of a subject have differences in cell morphology and/or function due to varied analyte levels (e.g., gene and/or protein expression) within the different cells. The specific position of a cell within a tissue (e.g., the cell's position relative to neighboring cells or the cell's position relative to the tissue microenvironment) can affect, e.g., the cell's morphology, differentiation, fate, viability, proliferation, behavior, and signaling and cross-talk with other cells in the tissue.

Spatial heterogeneity has been previously studied using techniques that only provide data for a small handful of analytes in the contact of an intact tissue or a portion of a tissue, or provide a lot of analyte data for single cells, but fail to provide information regarding the position of the single cell in a parent biological sample (e.g., tissue sample).

Furthermore, imaging systems used on spatial analyte data are inherently variable in their resolution and sensitivity. This is due in large part to the variability of manufacturers for imaging system components in addition to the arrangement of the imaging apparatus, differences between various types of imaging apparatuses, and image acquisition softwares. The image quality is further impacted by alterations in the image acquisition performed by the user. This problem becomes more apparent when trying to image samples of an unknown fluorescent intensity or by having samples imaged by users of varying experience.

Furthermore, in a laboratory environment, a variety of processing protocols are used to prepare a sample for analysis. These protocols can be performed in test tubes, on slides, or more generally, on a sample that is supported by a substrate. Certain protocols are performed at a stable, controlled temperatures to ensure the fidelity of the sample and protocol reagents. Other protocols involve temperature cycling and other steps in which the temperature of the sample is adjusted in controlled fashion. To heat the sample and its supporting substrate during a protocol, a thermocycler, heating plate, or other heating device may be used. As one example, thermocyclers can be as part of polymerase chain reaction protocols for nucleic acid amplification and in transcription and reverse transcription analytical sequences. Controlled heating of samples in thermocyclers and other heating devices also can occur to facilitate temperature-sensitive reactions for restriction enzyme digestion and rapid diagnostics, for example.

In addition, a biological sample may be placed on a solid support to be analyzed for identification or characterization of an analyte, such as DNA, RNA or other genetic material, within the sample. Printed guides may help improve placement of a sample on a solid support.

SUMMARY

The control slides, methods, and systems for assessing the quality and resolution of the imaging apparatuses and imaging systems can be implemented using a variety of substrates. As used herein, the term "substrate" refers to a support having a surface (e.g., a glass slide, a hydrogel, a film, a layer, a porous membrane, a flow cell, a solid material, or the like). In an embodiment, a substrate is a glass slide. A "substrate" as used herein, and when not preceded by the modifiers "chemical" or "sequence analysis," refers to a member with at least one surface that generally functions to provide physical support for biological samples, analytes, and/or any of the other chemical and/or physical moieties, agents, and structures, e.g., arrays, described herein. Substrates can be formed from a variety of solid materials, gel-based materials, colloidal materials, semi-solid materials (e.g., materials that are at least partially cross-linked), materials that are fully or partially cured, and materials that undergo a phase change or transition to provide physical support. Examples of substrates that can be used in the methods and systems described herein include, but are not limited to, slides (e.g., slides formed from various glasses, slides formed from various polymers), hydrogels, layers and/or films, membranes (e.g., porous membranes), flow cells, cuvettes, wafers, plates. In some embodiments, substrates can optionally include functional elements such as recesses, protruding structures, microfluidic elements (e.g., channels, reservoirs, electrodes, valves, seals), and various markings, as will be discussed in further detail below.

This disclosure further describes devices for holding or supporting substrates. In particular, the devices described include a first and second members that receive a first and second substrate, respectively. In some embodiments, the devices of the disclosure can be used for sandwiching the first and second substrates together for spatial transcriptomics applications. In some embodiments, the first substrate can support a sample (e.g., a biological substrate) on its surface. In some embodiments, the second substrate can include a plurality of barcoded probes and/or permeabilization reagents.

The devices for holding or supporting substrates described further include an alignment mechanism that is connected to at least one of the members and aligns the first and second members. Thus, the devices of the disclosure can advantageously align the first substrate and the second substrate and any samples, barcoded probes, or permeabilization reagents that may be on the surface of the first and second substrates. That is, the devices of the disclosure can facilitate analysis of a sample (e.g., a biological sample) by bringing the first and second substrates into contact with each other in an aligned manner. Alignment of the first and second substrates is key in spatial transcriptomics applications as the sample (e.g., a biological sample) may be required to be aligned with a barcoded area of a substrate.

Current methods of aligning biological samples with barcoded areas in spatial transcriptomics assays involve a user carefully placing the biological sample onto a substrate that includes a plurality of barcoded probes. Thus, in some embodiments, an advantage of the devices described is providing an alignment tool for users to align a sample with a barcoded area. The devices of the disclosure can reduce user error during the assay analysis, thereby also reducing sample analysis costs. In some embodiments, another advantage of the devices of the disclosure is a reduction in the number of aberrations or imaging imperfections that may arise due to user error in aligning a biological sample with a barcoded area of the substrate. In some embodiments, the devices of the disclosure allow for pre-screening of samples for areas of interest. In some embodiments, the devices of the disclosure allow for archived samples to be examined.

In one aspect, this disclosure is directed to a sample holder, including a first member including a first retaining mechanism configured to retain a first substrate including a sample, a second member including a second retaining mechanism configured to retain a second substrate including a reagent medium, and an alignment mechanism connected to one or both of the first and second members, and configured to align the first and second members such that the sample contacts at least a portion of the reagent medium when the first and second members are aligned.

In some embodiments, the alignment mechanism includes a rotating actuator connected to the first and second members. In some embodiments, the alignment mechanism includes one or more connectors positioned on one or both of the first and second members, and one or more receivers positioned on one or both of the first and second members, wherein the one or more receivers are positioned to engage with the one or more connectors. In some embodiments, the rotating actuator includes a hinge. In some embodiments, the rotating actuator includes a folding member. In some embodiments, the rotating actuator includes at least one arm. In some embodiments, the first retaining mechanism includes a recess dimensioned to receive the first substrate. In some embodiments, the sample holder further includes a gasket positioned within the recess and configured to maintain an interference fit between the recess and the first substrate. In some embodiments, the first retaining mechanism includes one or more members configured to apply a force to the first substrate to maintain contact between the first substrate and the first member.

In some embodiments, the second retaining mechanism includes a recess dimensioned to receive the second substrate. In some embodiments, the second retaining mechanism includes one or more members configured to apply a force to the second substrate to maintain contact between the second substrate and the second member. In some embodiments, the reagent medium includes at least one of: a solution including a permeabilization reagent, a solid permeabilization reagent, and a hydrogel compound including a permeabilization reagent. In some embodiments, the first member includes an aperture positioned so that when the first substrate is retained, the aperture is aligned with a sample region of the first substrate. In some embodiments, the second member includes at least one aperture positioned so that when the first substrate is retained and the first and second members are aligned by the alignment mechanism, an aperture of the at least one aperture is aligned with at least a portion of a sample region of the first substrate.

In some embodiments, the sample holder further includes a reagent well formed by one or more bounding surfaces of the at least one aperture and by a back surface of the second substrate, wherein a reagent solution added to the reagent well is contained by the bounding surfaces and permeates through the back surface of the second substrate. In some embodiments, the back surface of the second substrate is opposite to a front surface of the second substrate that faces the sample on the first substrate. In some embodiments, the sample holder further includes a first adjustment mechanism connected to the first member and configured to translate the first substrate in at least one direction parallel to a surface of the first substrate that supports the sample. In some embodiments, the alignment mechanism is configured to maintain a separation between the first and second substrates when the first and second substrates are aligned. In some embodiments, the alignment mechanism is configured to maintain the separation such that at least a portion of the sample on the first substrate contacts at least a portion of the reagent medium on the second substrate. In some embodiments, the separation between the first and second substrates is between 50 microns and 1 mm, measured in a direction orthogonal to a surface of the first substrate that supports the sample. In some embodiments, the separation between the first and second substrates is between 2.5 microns and 25 microns, measured in a direction orthogonal to a surface of the first substrate that supports the sample.

In some embodiments, the separation between the first and second substrates is between 50 microns and 500 microns. In some embodiments, the alignment mechanism is configured to maintain the first and second substrates approximately parallel when the first and second substrates are aligned so that an angle between the first and second substrates is two degrees or less. In some embodiments, the angle is 0.5 degrees or less. In some embodiments, the sample holder further includes one or more spacing members connected to one or both of the first and second members positioned so that when the first and second substrates are aligned, the one or more spacing members are between the first and second members. In some embodiments, the sample holder further includes a second adjustment mechanism configured to adjust a distance of the separation in direction orthogonal to a surface of the first substrate that supports the sample. In some embodiments, the second adjustment mechanism is a component of the alignment mechanism. In some embodiments, the second adjustment mechanism is connected to one or both of the first member and the second member.

In another aspect, this disclosure is directed to a sample holder. The sample holder includes a first member including a first retaining mechanism configured to retain a first substrate including a sample. The sample holder further includes a second member including a second retaining mechanism configured to retain a second substrate including an array. The sample holder further includes an alignment mechanism connected to one or both of the first and second members. The alignment mechanism configured to align the first and second members such that at least a portion of the sample is vertically aligned with at least a portion of the array when the first and second members are aligned.

In some embodiments, the sample includes an analyte in a spatial arrangement. In some embodiments, the sample holder further includes one or more spacing members connected to one or both of the first and second members positioned so that when the first and second substrates are aligned, the one or more spacing members are between the first and second members and/or between the first and second substrates and are configured to provide a minimum spacing between the first substrate and the second substrate. In some embodiments, the first member further includes a second first retaining mechanism configured to retain a second first substrate comprising a second sample. In some embodiments, the alignment mechanism is further configured to align the first and second members such that the second sample is vertically aligned with at least a portion of a second array of the second substrate when the first and second members are aligned. . . . In some embodiments, the first substrate, the second substrate, and the one or more spacing members form a chamber when the first and second members are aligned. In some embodiments, the second member includes at least one aperture positioned so that when the first substrate is retained and the first and second members are aligned by the alignment mechanism, an aperture of the at least one aperture is aligned with at least a portion of a sample region of the first substrate and/or at least the portion the array.

In some embodiments, the sample holder further includes a reagent well formed by one or more bounding surfaces of the at least one aperture and by a back surface of the second member. In some embodiments, a reagent solution added to the reagent well is contained by the bounding surfaces and travels from the reagent well to contact the sample when the first and second members are aligned. In some embodiments, the reagent well includes a port configured to receive the reagent solution. In some embodiments, the port includes a one-way valve. In some embodiments, the first member includes at least one first aperture positioned so that when the first substrate is retained and the first and second members are aligned by the alignment mechanism, a first aperture of the at least one first aperture is aligned with at least a portion of a sample region of the first substrate and/or at least the portion the array. In some embodiments, the sample holder further includes a first reagent well formed by one or more bounding surfaces of the at least one first aperture and by a surface of the first member, wherein a reagent solution added to the first reagent well is contained by the bounding surfaces and travels from the first reagent well to contact the sample when the first and second members are aligned. In some embodiments, the first reagent well includes a port configured to receive the reagent solution.

In some embodiments, the second member includes a second aperture of the at least one aperture. The second aperture may be configured to remove the reagent solution from the second member. In some embodiments, the one or more spacing members includes a first spacing member coupled to the first member and/or the first substrate and a second spacing member coupled to the second member and/or the second substrate. In some embodiments, the first spacing member includes a thickness greater than the second spacing member. In some embodiments, the first substrate, the second substrate, the first spacing member, and the second spacing member form a chamber when the first and second members are aligned. In some embodiments, the chamber includes a flow cell. In some embodiments, the second member includes a removable portion, the removable portion including the second substrate. In some embodiments, the first substrate includes a histology slide. In some embodiments, the second substrate includes a slide comprising the array. In some embodiments, the sample holder further includes the first substrate and the second first substrate.

In another aspect, this disclosure is directed to a system. The system includes the sample holder of any one of the preceding embodiments and a thermocycler.

In another aspect, this disclosure is directed to a method of preparing a biological sample for spatial analysis. The method includes providing a sample holder. The sample holder includes a first member including a first retaining mechanism configured to retain a first substrate including the biological sample. The sample holder further includes a second member including a second retaining mechanism configured to retain a second substrate including an array. The sample holder further includes an alignment mechanism connected to one or both of the first and second members, and configured to align the first and second members such that the sample is vertically aligned with at least a portion of the array when the first and second members are aligned. The method further includes positioning the first substrate including the biological sample in the first retaining mechanism of the first member. The method further includes, via the alignment mechanism, manually aligning the first and second members such that at least a portion of the sample is vertically aligned with at least a portion of the array when the first and second members are aligned. The method further includes migrating an analyte from the vertically aligned portion of the sample to the portion of the array.

In some embodiments, positioning the first substrate includes positioning the first substrate in the first retaining mechanism such that the biological sample is aligned with an array area indicator on a surface of the first retaining mechanism. In some embodiments, positioning the first substrate includes positioning the first substrate in the first retaining mechanism when the first member is in an open position relative to the second member and wherein the manual alignment of the first and second members comprises closing the first member over the second member. In some embodiments, migrating the analyte includes migrating the analyte through a reagent medium that contacts the aligned portion of the biological sample and the array. In some embodiments, the method further includes adding, responsive to the manual aligning, the reagent medium to the sample holder through a port in the second member. In some embodiments, the method further includes adding, prior to the manual aligning, the reagent medium to a surface of the second substrate. In some embodiments, the method further includes introducing the sample holder in a thermocycler to promote capture of the analyte during the migrating. In some embodiments, the method further includes positioning the second substrate in the second retaining mechanism.

All publications, patents, patent applications, and information available on the internet and mentioned in this specification are herein incorporated by reference to the same extent as if each individual publication, patent, patent application, or item of information was specifically and individually indicated to be incorporated by reference. To the extent publications, patents, patent applications, and items of information incorporated by reference contradict the disclosure contained in the specification, the specification is intended to supersede and/or take precedence over any such contradictory material.

Where values are described in terms of ranges, it should be understood that the description includes the disclosure of all possible sub-ranges within such ranges, as well as specific numerical values that fall within such ranges irrespective of whether a specific numerical value or specific sub-range is expressly stated.

The term "each," when used in reference to a collection of items, is intended to identify an individual item in the collection but does not necessarily refer to every item in the collection, unless expressly stated otherwise, or unless the context of the usage clearly indicates otherwise.

Various embodiments of the features of this disclosure are described herein. However, it should be understood that such embodiments are provided merely by way of example, and numerous variations, changes, and substitutions can occur to those skilled in the art without departing from the scope of this disclosure. It should also be understood that various alternatives to the specific embodiments described herein are also within the scope of this disclosure.

DESCRIPTION OF DRAWINGS

The following drawings illustrate certain embodiments of the features and advantages of this disclosure. These embodiments are not intended to limit the scope of the appended claims in any manner. Like reference symbols in the drawings indicate like elements.

Like reference symbols in the various drawings indicate like elements.

DETAILED DESCRIPTION

I. Introduction

Figure 1:
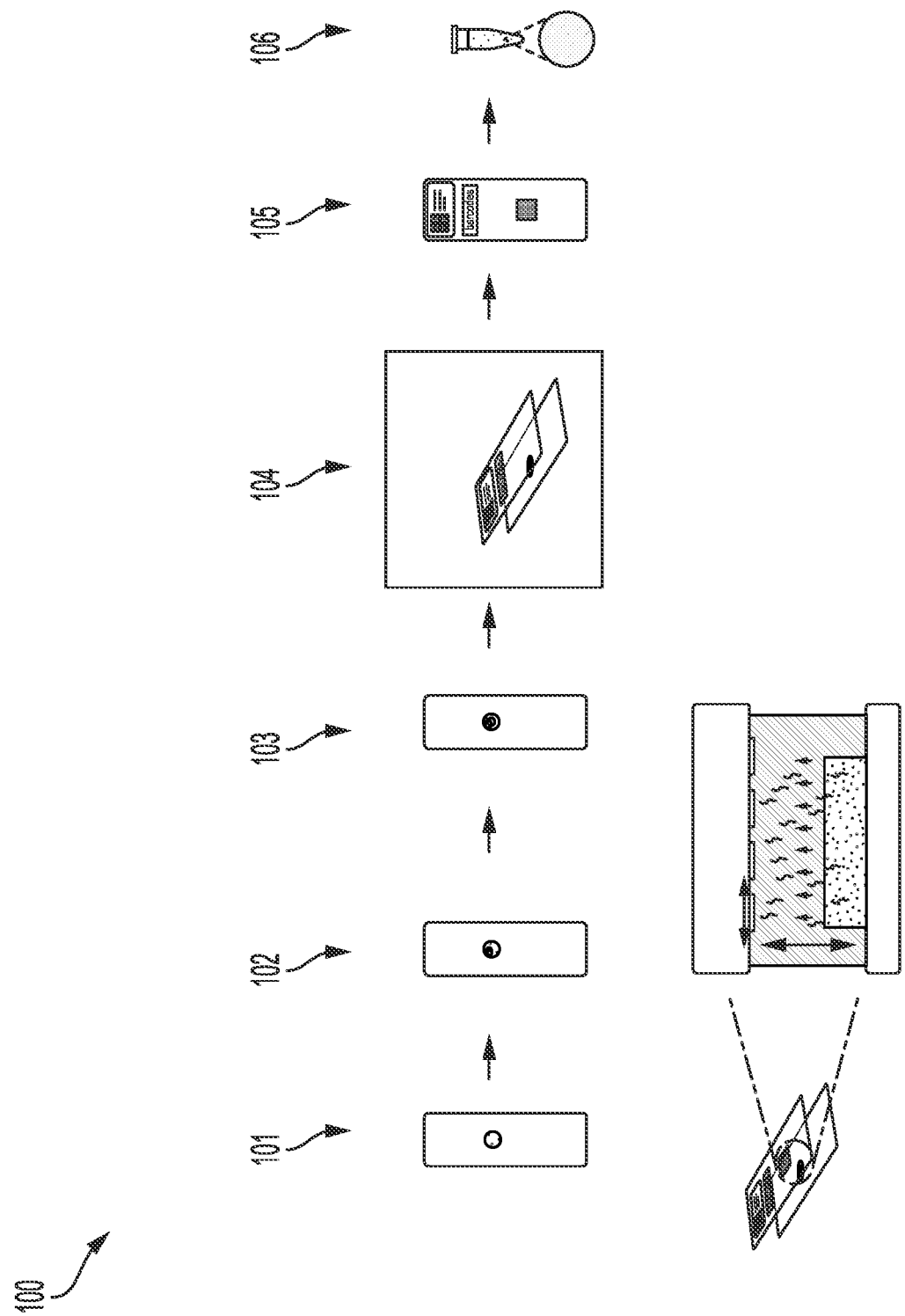
FIG. 1 shows an exemplary spatial analysis workflow in accordance with some example implementations.

This disclosure describes apparatus, systems, methods, and compositions for spatial analysis of biological samples. This section describes certain general terminology, analytes, sample types, and preparative steps that are referred to in later sections of the disclosure.

This disclosure describes apparatus, systems, methods, and compositions for spatial analysis of biological samples. This section describes certain general terminology, analytes, sample types, and preparative steps that are referred to in later sections of the disclosure. For example, the terms and phrases: spatial analysis, barcode, nucleic acid, nucleotide, probe, target, oligonucleotide, polynucleotide, subject, genome, adaptor, adapter, tag, hybridizing, hybridize, annealing, anneal, primer, primer extension, proximity ligation, nucleic acid extension, polymerase chain reaction (PCR) amplification, antibody, affinity group, label, detectable label, optical label, template switching oligonucleotide, splint oligonucleotide, analytes, biological samples, general spatial array-based analytical methodology, spatial analysis methods, immunohistochemistry and immunofluorescence, capture probes, substrates, arrays, analyte capture, partitioning, analysis of captured analytes, quality control, and/or the like are described in more detail in PCT Patent Application Publication No. WO2020/123320, the entire contents of which are incorporated herein by reference.

(a) Spatial Analysis

Tissues and cells can be obtained from any source. For example, tissues and cells can be obtained from single-cell or multicellular organisms (e.g., a mammal). Tissues and cells obtained from a mammal, e.g., a human, often have varied analyte levels (e.g., gene and/or protein expression) which can result in differences in cell morphology and/or function. The position of a cell within a tissue can affect, e.g., the cell's fate, behavior, morphology, and signaling and cross-talk with other cells in the tissue. Information regarding the differences in analyte levels (gene and/or protein expression) within different cells in a tissue of a mammal can also help physicians select or administer a treatment that will be effective in the single-cell or multicellular organisms (e.g., a mammal) based on the detected differences in analyte levels within different cells in the tissue. Differences in analyte levels within different cells in a tissue of a mammal can also provide information on how tissues (e.g., healthy and diseased tissues) function and/or develop. Differences in analyte levels within different cells in a tissue of a mammal can also provide information of different mechanisms of disease pathogenesis in a tissue and mechanism of action of a therapeutic treatment within a tissue. Differences in analyte levels within different cells in a tissue of a mammal can also provide information on drug resistance mechanisms and the development of the same in a tissue of a mammal. Differences in the presence or absence of analytes within different cells in a tissue of a multicellular organism (e.g., a mammal) can provide information on drug resistance mechanisms and the development of the same in a tissue of a multicellular organism.

The spatial analysis methodologies herein provide for the detection of differences in an analyte level (e.g., gene and/or protein expression) within different cells in a tissue of a mammal or within a single cell from a mammal. For example, spatial analysis methodologies can be used to detect the differences in analyte levels (e.g., gene and/or protein expression) within different cells in histological slide samples, the data from which can be reassembled to generate a three-dimensional map of analyte levels (e.g., gene and/or protein expression) of a tissue sample obtained from a mammal, e.g., with a degree of spatial resolution (e.g., single-cell resolution).

Spatial heterogeneity in developing systems has typically been studied via RNA hybridization, immunohistochemistry, fluorescent reporters, or purification or induction of pre-defined subpopulations and subsequent genomic profiling (e.g., RNA-seq). Such approaches, however, rely on a relatively small set of pre-defined markers, therefore introducing selection bias that limits discovery. These prior approaches also rely on a priori knowledge. Spatial RNA assays traditionally relied on staining for a limited number of RNA species. In contrast, single-cell RNA-sequencing allows for deep profiling of cellular gene expression (including non-coding RNA), but the established methods separate cells from their native spatial context.

Current spatial analysis methodologies provide a vast amount of analyte level and/or expression data for a variety of multiple analytes within a sample at high spatial resolution, e.g., while retaining the native spatial context. Spatial analysis methods include, e.g., the use of a capture probe including a spatial barcode (e.g., a nucleic acid sequence that provides information as to the position of the capture probe within a cell or a tissue sample (e.g., mammalian cell or a mammalian tissue sample) and a capture domain that is capable of binding to an analyte (e.g., a protein and/or nucleic acid) produced by and/or present in a cell. As described herein, the spatial barcode can be a nucleic acid that has a unique sequence, a unique fluorophore or a unique combination of fluorophores, a unique amino acid sequence, a unique heavy metal or a unique combination of heavy metals, or any other unique detectable agent. The capture domain can be any agent that is capable of binding to an analyte produced by and/or present in a cell (e.g., a nucleic acid that is capable of hybridizing to a nucleic acid from a cell (e.g., an mRNA, genomic DNA, mitochondrial DNA, or miRNA), a substrate including an analyte, a binding partner of an analyte, or an antibody that binds specifically to an analyte). A capture probe can also include a nucleic acid sequence that is complementary to a sequence of a universal forward and/or universal reverse primer. A capture probe can also include a cleavage site (e.g., a cleavage recognition site of a restriction endonuclease), a photolabile bond, a thermosensitive bond, or a chemical-sensitive bond.

The binding of an analyte to a capture probe can be detected using a number of different methods, e.g., nucleic acid sequencing, fluorophore detection, nucleic acid amplification, detection of nucleic acid ligation, and/or detection of nucleic acid cleavage products. In some examples, the detection is used to associate a specific spatial barcode with a specific analyte produced by and/or present in a cell (e.g., a mammalian cell).

Capture probes can be, e.g., attached to a surface, e.g., a solid array, a bead, or a coverslip. In some examples, capture probes are not attached to a surface. In some examples, capture probes can be encapsulated within, embedded within, or layered on a surface of a permeable composition (e.g., any of the substrates described herein). For example, capture probes can be encapsulated or disposed within a permeable bead (e.g., a gel bead). In some examples, capture probes can be encapsulated within, embedded within, or layered on a surface of a substrate (e.g., any of the exemplary substrates described herein, such as a hydrogel or a porous membrane).

In some examples, a cell or a tissue sample including a cell are contacted with capture probes attached to a substrate (e.g., a surface of a substrate), and the cell or tissue sample is permeabilized to allow analytes to be released from the cell and bind to the capture probes attached to the substrate. In some examples, analytes released from a cell can be actively directed to the capture probes attached to a substrate using a variety of methods, e.g., electrophoresis, chemical gradient, pressure gradient, fluid flow, or magnetic field.

In other examples, a capture probe can be directed to interact with a cell or a tissue sample using a variety of methods, e.g., inclusion of a lipid anchoring agent in the capture probe, inclusion of an agent that binds specifically to, or forms a covalent bond with a membrane protein in the capture probe, fluid flow, pressure gradient, chemical gradient, or magnetic field.

Non-limiting aspects of spatial analysis methodologies are described in WO 2011/127099, WO 2014/210233, WO 2014/210225, WO 2016/162309, WO 2018/091676, WO 2012/140224, WO 2014/060483, U.S. Pat. Nos. 10,002,316, 9,727,810, U.S. Patent Application Publication No. 2017/0016053, Rodriques et al., *Science* 363(6434): 1463-1467, 2019; WO 2018/045186, Lee et al., *Nat. Protoc.* 10(3):442-458, 2015: WO 2016/007839, WO 2018/045181, WO 2014/163886, Trejo et al., *PLOS ONE* 14(2):e0212031, 2019, U.S. Patent Application Publication No. 2018/0245142, Chen et al., *Science* 348(6233): aaa6090, 2015, Gao et al., *BMC Biol.* 15:50, 2017, WO 2017/144338, WO 2018/107054, WO 2017/222453, WO 2019/068880, WO 2011/094669, U.S. Pat. Nos. 7,709,198, 8,604,182, 8,951,726, 9,783,841, 10,041,949, WO 2016/057552, WO 2017/147483, WO 2018/022809, WO 2016/166128, WO 2017/027367, WO 2017/027368, WO 2018/136856, WO 2019/075091, U.S. Pat. No. 10,059,990, WO 2018/057999, WO 2015/161173, and Gupta et al., *Nature Biotechnol.* 36:1197-1202, 2018, the entire contents of which are incorporated herein by reference and can be used herein in any combination. Further non-limiting aspects of spatial analysis methodologies are described herein.

Embodiments described herein may map the spatial gene expression of complex tissue samples (e.g., on tissue slides) with slides (e.g., gene expression slides) that utilize analyte and/or mRNA transcript capture and spatial barcoding technology for library preparation. A tissue (e.g., fresh-frozen, formalin-fixed paraffin-embedded (FFPE), or the like) may be sectioned and placed in proximity to a slide with thousands of barcoded spots, each containing millions of capture oligonucleotides with spatial barcodes unique to that spot. Once tissue sections are fixed, stained, and permeabilized, they release mRNA which binds to capture oligos from a proximal location on the tissue. A reverse transcription reaction may occur while the tissue is still in place, generating a cDNA library that incorporates the spatial barcodes and preserves spatial information. Barcoded cDNA libraries are mapped back to a specific spot on a capture area of the barcoded spots. This gene expression data may be subsequently layered over a high-resolution microscope image of the tissue section, making it possible to visualize the expression of any mRNA, or combination of mRNAs, within the morphology of the tissue in a spatially-resolved manner.

FIG. 1 shows an exemplary spatial analysis workflow 100 in accordance with some example implementations. The workflow 100 includes, at 101, preparing a biological sample on a slide (e.g., a pathology slide), fixing the sample, and/or staining 102 the biological sample for imaging. The stained sample can be then imaged on the slide using brightfield (to image the sample hematoxylin and eosin stain) and/or fluorescence (to image features) modalities. The imaging may include high resolution imaging (e.g., images that can disclose pathological and histological features). Optionally, at 103, the sample can be destained prior to permeabilization. At 104, a permeabilization solution may be applied to biological sample while the pathology slide is aligned in a "sandwich" configuration with a slide comprising a spatially barcoded array (e.g., on a GEx slide). The permeabilization solution allowing the analyte and/or mRNA transcripts to migrate away from the sample, diffuse across the permeabilization solution, and toward the array. The analyte and/or mRNA transcripts interacts with a capture probe on the spatially-barcoded array on the slide.

At 105, the capture probes can be optionally cleaved from the array, and the captured analytes can be spatially-barcoded by performing a reverse transcriptase first strand cDNA reaction. A first strand cDNA reaction can be optionally performed using template switching oligonucleotides. At 106, the first strand cDNA can be amplified (e.g., using polymerase chain reaction (PCR)), where the forward and reverse primers flank the spatial barcode and analyte regions of interest, generating a library associated with a particular spatial barcode. In some embodiments, the cDNA comprises a sequencing by synthesis (SBS) primer sequence. The library amplicons may be sequenced and analyzed to decode spatial information.

Figure 2:
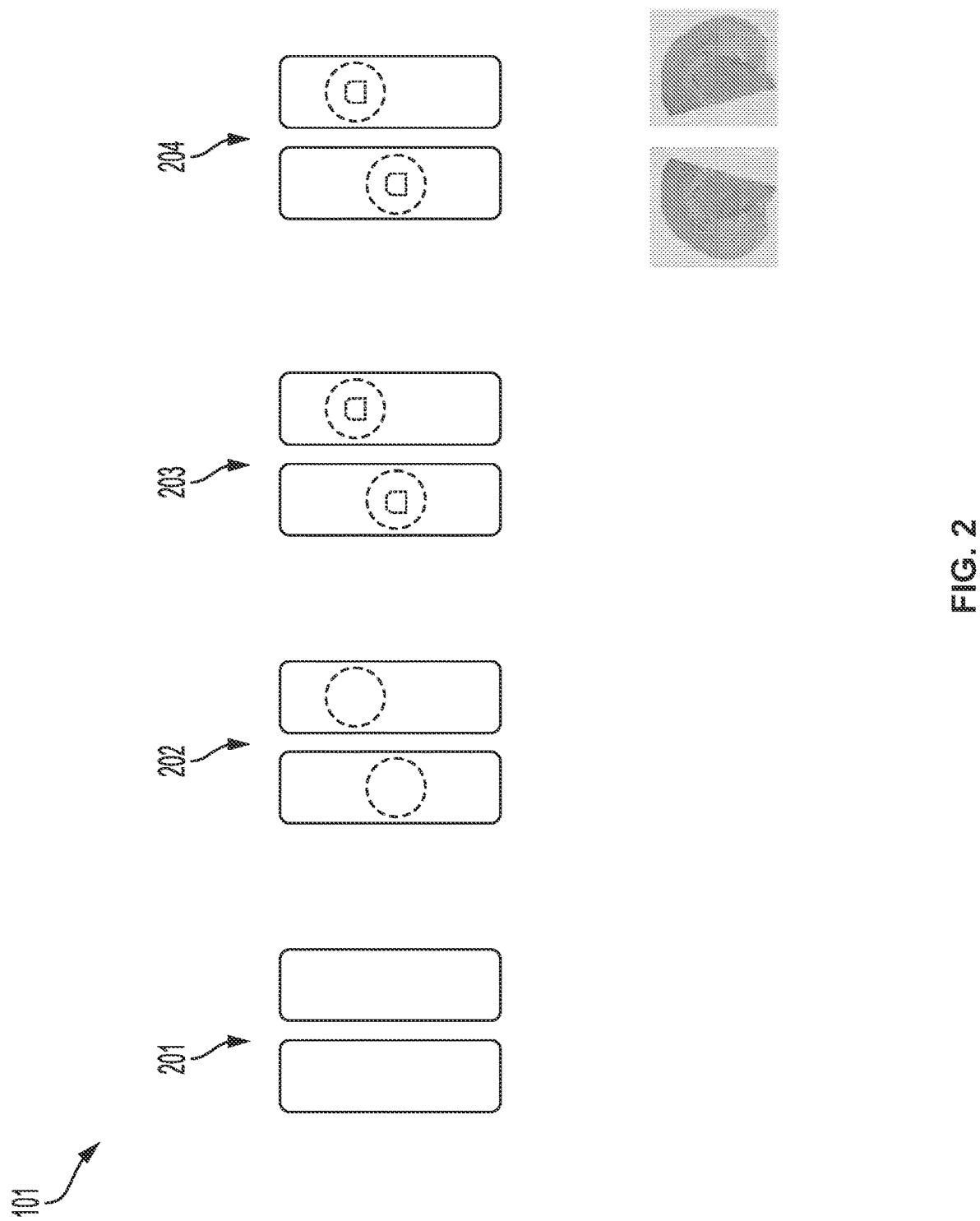
FIG. 2 depicts an example workflow for preparing the biological sample on a slide in accordance with some example implementations.

FIG. 2 depicts an example workflow 101 for preparing the biological sample on the slide (e.g., a pathology slide) in accordance with some example implementations. Preparing the biological sample on the slide may include selecting a pathology glass slide 201. The workflow 101 further includes placing tissue sections on the glass slide 202. Placing tissue sections on the glass slide may include placing the tissue anywhere on the glass slide including placing the tissue on or in relation to a fiducial disposed on the glass slide. The fiducial may include any marking to aid in placement of the tissue on the slide and/or aid in the alignment of the tissue slide relative to the gene expression slide. The workflow 101 further includes staining the tissue with hematoxylin and eosin 203 or another staining agent or method. The workflow 101 further includes imaging the tissue 204 on the slide using brightfield (to image the sample hematoxylin and eosin stain) or another imaging technique. The imaging may include high resolution imaging on a user imaging system. The imaging may allow the user to confirm the relevant pathology and/or identify any target areas for analysis.

Embodiments described herein relating to preparing the biological sample on the slide may beneficially allow a user to confirm pathology or relevant regions on a tissue section, to confirm selection of best or undamaged tissue sections for analysis, to improve array-tissue alignment by allowing placement anywhere on the pathology slide. Further, workflows for preparing the biological sample on the slide may empower user or scientists to choose what to sequence (e.g., what tissue section(s) to sequence).

Figure 3:
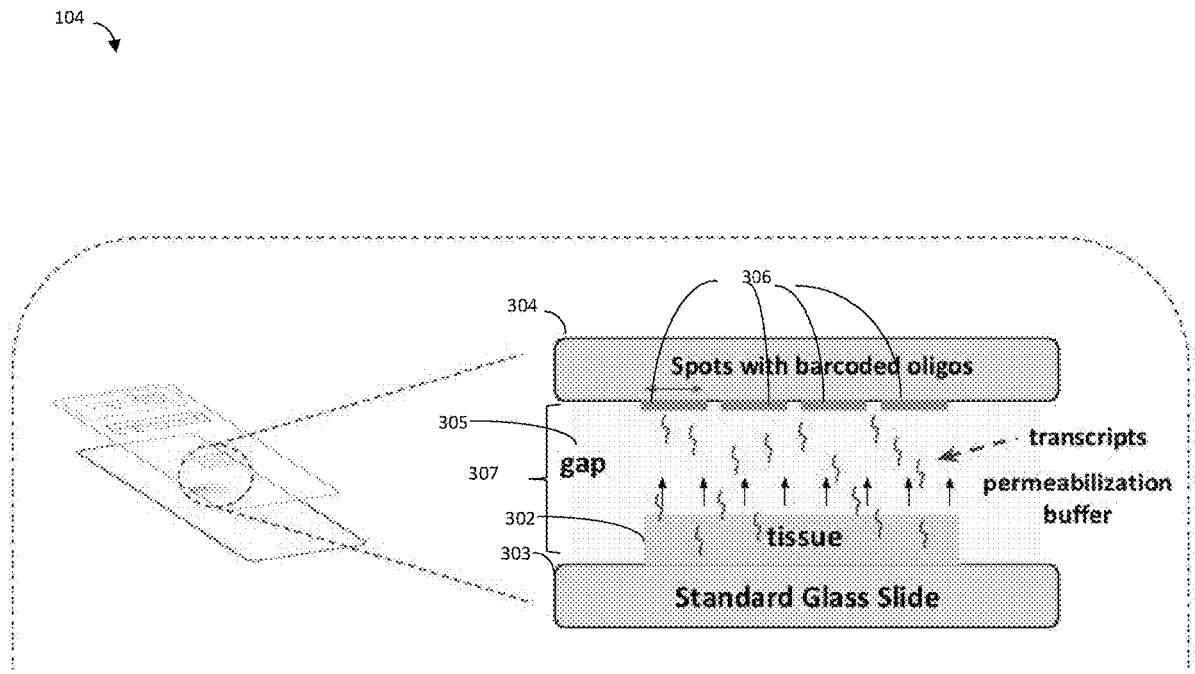
FIG. 3 is a schematic diagram depicting an exemplary permeabilization solution interaction between a tissue slide and a gene expression slide in a sandwich configuration in accordance with some example implementations.

FIG. 3 is a schematic diagram depicting an exemplary permeabilization solution interaction 104 between a tissue slide and a gene expression slide in a sandwich configuration in accordance with some example implementations. In the exemplary configuration, a sample (a tissue or biological sample) 302 is disposed on the slide 303 (e.g., a pathology slide or a histology slide) and is sandwiched between the slide 303 and a slide 304 (e.g., gene expression slide) that is populated with spatially-barcoded capture probes 306. As shown, the slide 304 is in a superior position to the pathology slide 303. In some embodiments, the slide 303 may be positioned superior to the slide 304. When a permeabilization solution 305 is applied to a gap 307 between the slide 303 and the slide 304, the permeabilization solution 305 creates a permeabilization buffer which permeabilizes or digests the sample 302 and the analytes and/or mRNA transcripts 308 of the tissue sample 302 may release, diffuse across the gap 307 toward the capture probes 306, and bind on the capture probes 306. After the transcripts 308 bind on the capture probes 306, a reverse transcription reaction may occur, generating a cDNA library associated with a particular spatial barcode. Barcoded cDNA libraries may be mapped back to a specific spot on a capture area of the capture probes 306. This gene expression data may be subsequently layered over a high-resolution microscope image of the tissue section ((e.g., taken at 204 of FIG. 2), making it possible to visualize the expression of any mRNA, or combination of mRNAs, within the morphology of the tissue in a spatially-resolved manner.

The sandwich configuration of the sample 302, the slide 303, and the slide 304 may provide advantages over other methods of spatial analysis and/or analyte capture. For example, the sandwich configuration may reduce a burden of users to develop in house tissue sectioning and/or tissue mounting expertise. Further, the sandwich configuration may decouple sample preparation/tissue imaging from the barcoded array (e.g., spatially-barcoded capture probes 306) and enable selection of a particular region of interest of analysis (e.g., for a tissue section larger than the barcoded array). The sandwich configuration also beneficially enables spatial transcriptomics assays without having to place a tissue section 302 directly on the gene expression slide (e.g., slide 304) which may reduce cost and risk of mistakes/issues during sample preparation. The sandwich configuration may also provide an improvement of sensitivity and spatial resolution by vertically confining target molecules within the diffusion distance.

(b) Substrate Holder

Described herein are methods in which an array with capture probes located on a substrate and a biological sample located on a different substrate, are contacted, or brought into proximity, such that the array is in contact with portions (e.g., analytes or other molecules) the biological sample (e.g., the substrates are sandwiched together). In some embodiments, the array and the biological sample can be contacted (e.g., sandwiched), without the aid of a substrate holder. In some embodiments, the array and biological sample substrates can be placed in a substrate holder (e.g., an array alignment device) designed to align the biological sample and the array. For example, the substrate holder can have placeholders for one or more substrates. In some embodiments, an array including capture probes can be positioned on one side of the substrate holder (e.g., in a first substrate placeholder). In some embodiments, a biological sample can be placed on the adjacent side of the substrate holder in a second placeholder.

In some embodiments, a hinge can be located between the two substrate placeholders that allows the substrate holder to close, e.g., make a sandwich between the two substrate placeholders. In some embodiments, when the substrate holder is closed the biological sample and the array with capture probes are contacted with one another under conditions sufficient to allow analytes present in the biological sample to interact with the capture probes of the array. For example, dried permeabilization reagents can be placed on the biological sample and rehydrated. A permeabilization solution can be flowed through the substrate holder to permeabilize the biological sample and allow analytes in the biological sample to interact with the capture probes. Additionally, the temperature of the substrates or permeabilization solution can be used to initiate or control the rate of permeabilization. For example, the substrate including the array, the substrate including the biological sample, or both substrates can be held at a low temperature to slow diffusion and permeabilization efficiency. Once sandwiched, in some embodiments, the substrates can be heated to initiate permeabilization and/or increase diffusion efficiency. Transcripts that are released from the permeabilized tissue can diffuse to the array and be captured by the capture probes. The sandwich can be opened, and cDNA synthesis can be performed on the array.

Any of the variety of combinations described herein where a sandwich including an array with capture probes and a biological sample on two different substrates can be placed in a substrate holder designed to align the biological sample and the array. For example, the substrate holder can have placeholders for one or more substrates. In some embodiments, an array including capture probes can be positioned on one side of the substrate holder (e.g., in a first substrate placeholder). In some embodiments, a biological sample can be placed on the adjacent side of the substrate holder in a second placeholder. In some embodiments, in between the two substrate placeholders can be a hinge that allows the substrate holder to close, e.g., make a sandwich between the two substrate placeholders. In some embodiments, when the substrate holder is closed the biological sample and the array with capture probes can be contacted with one another under conditions sufficient to allow analytes present in the biological sample to interact with the capture probes of the array for spatial analysis by any method described herein. For example, dried permeabilization reagents can be placed on the biological sample and rehydrated. Additionally, a permeabilization solution can be flowed through the substrate holder to permeabilize the biological sample and allow analytes in the biological sample to interact with the capture probes.

In some embodiments, a flexible array described herein can be placed in the substrate holder, and sandwiched with a biological sample. In some embodiments, the flexible array can include spatially-barcoded cross-linked features. In some embodiments, the flexible array can be presoaked in permeabilization reagents before being placed into the substrate holder. In some embodiments, the flexible array can be soaked in permeabilization reagents after being placed in the substrate holder. In some embodiments, the substrate holder including a biological sample in one placeholder and a flexible array can be closed (e.g., form a sandwich) such that the permeabilization reagents allow analytes present in the biological sample to interact with capture probes of the flexible array (e.g., capture probes on the spatially-barcoded features).

In some embodiments, the substrate holder can be heated or cooled to regulate permeabilization and/or diffusion efficiency.

II. Systems for Sample Analysis

The methods described above for analyzing biological samples can be implemented using a variety of hardware components. In this section, examples of such components are described. However, it should be understood that in general, the various steps and techniques discussed herein can be performed using a variety of different devices and system components, not all of which are expressly set forth.

The systems, methods, and computer readable mediums described herein can enable efficient and precise alignment of samples and arrays, thus facilitating the spatial transcriptomic imaging and analysis workflows or assays described herein. Samples, such as portions of tissue, can be placed on a first substrate. The first substrate can include a slide onto which a user can place a sample of the tissue. An array, such as a reagent array, can be formed on a second substrate. The second substrate can include a slide and the array can be formed on the second substrate. The use of separate substrates for the sample and the array can beneficially allow user to perform the spatial transcriptomic assays described herein without requiring the sample to be placed onto an array substrate. The sample holder and methods of use described herein can improve the ease by which users provide samples for spatial transcriptomic analysis. For example, the systems and methods described herein alleviate users from possessing advanced sample or tissue sectioning or mounting expertise. Additional benefits of utilizing separate substrates for samples and arrays can include improved sample preparation and sample imaging times, greater ability to perform region of interest (ROI) selection, and more efficient use of samples and array substrates. In some aspects, the region of interest may include an area where the biological sample 302 and the capture probes 306 overlap in a sandwich configuration.

Sample and Array Alignment Devices and Methods

Figure 4:
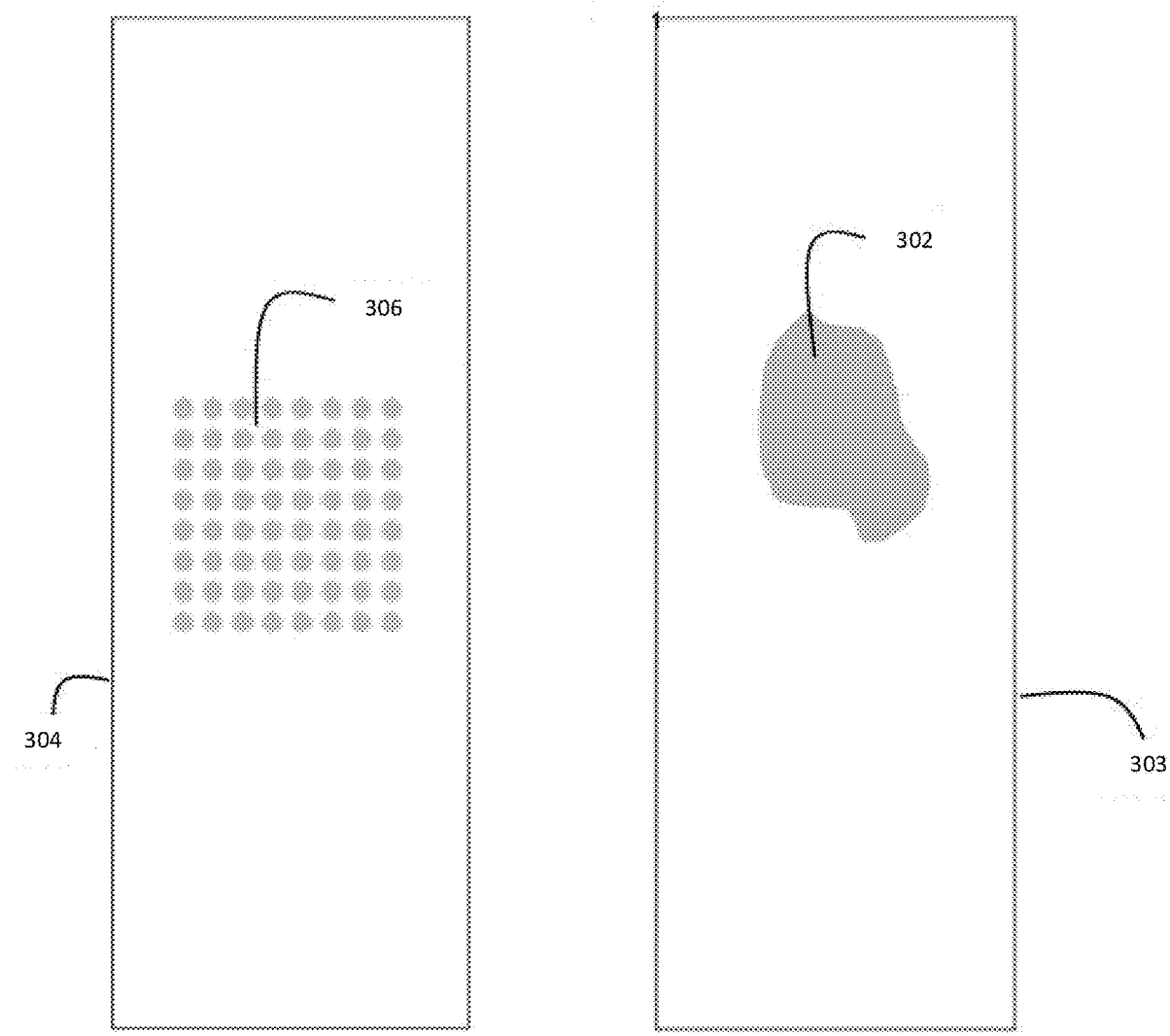
FIG. 4 is a schematic diagram showing a sample mounted on a first substrate and a feature array disposed on a second substrate in accordance with some example implementations.

Spatial analysis workflows generally involve contacting a sample with an array of features. In some embodiments, to achieve contact between the sample and the array, the sample is prepared on a first substrate (e.g., a slide) and the array is prepared on a second substrate (e.g., a slide), and the two slides are brought into proximity such that the sample on the first substrate is aligned with and contacts (e.g, via a permeabilization solution the feature array on the second substrate. FIG. 4 is a schematic diagram showing a sample 302 mounted on a first substrate (e.g., slide 303), and a feature array 306 disposed on a second substrate (e.g., slide 304).

In some workflows, the alignment and contacting operations are performed manually. However, manual alignment is prone to operator error and inconsistency: alignment operations between sample 302 and feature array 306 may be inconsistent and/or imperfect. Improper alignment of sample 302 and feature array 3066 can be disadvantageous for a number of reasons. For example, if the sample and array are imperfectly aligned when contact occurs, it may not be possible to successfully remove the sample and attempt re-alignment, and the array may be rendered unusable. For expensive feature arrays, this results in significant increased assay cost.

Further, certain assays involving imaging the sample through the feature array. If the sample and array are improperly aligned, imaging can be imperfect, and can be adversely affected by imperfections that arise from misalignment.

In addition, many tissue samples are available in archived (i.e., slide mounted) form. As a result, workflows that rely on direct physical placement of the tissue sample on a feature array may not be able to accommodate such samples. This limits the applicability of such workflows to only a subset of available samples.

The present disclosure features devices and methods for alignment of a sample 302 and a feature array 306. The devices and methods ensure correct alignment and contact between the sample and feature array so that reproducible spatial analyses can be conducted in a manner that is not significantly affected by systematic variations in alignment errors. The devices and methods reduce consumables waste (i.e., wasted feature arrays) and cost, and also reduce sample waste. In some embodiments, feature array 306 is includes printed spots, barcoded gels, barcoded microspheres, a gel film, or any combination thereof. The feature array 306 can also be a uniform coating of probes, such as in tissue optimization slides.

Figure 5A:
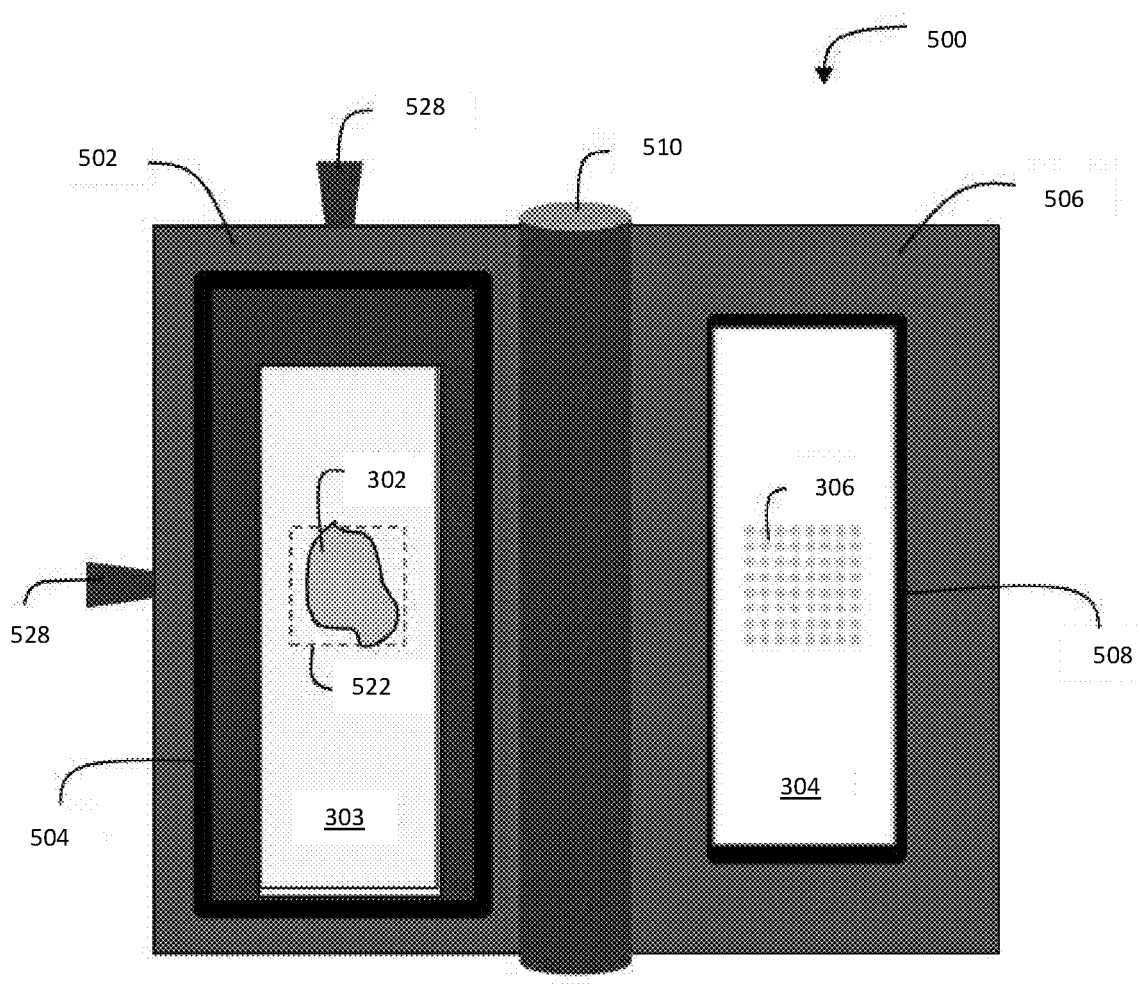
FIG. 5A is a schematic top view of an example of a sample holder in accordance with some example implementations.
Figure 5B:
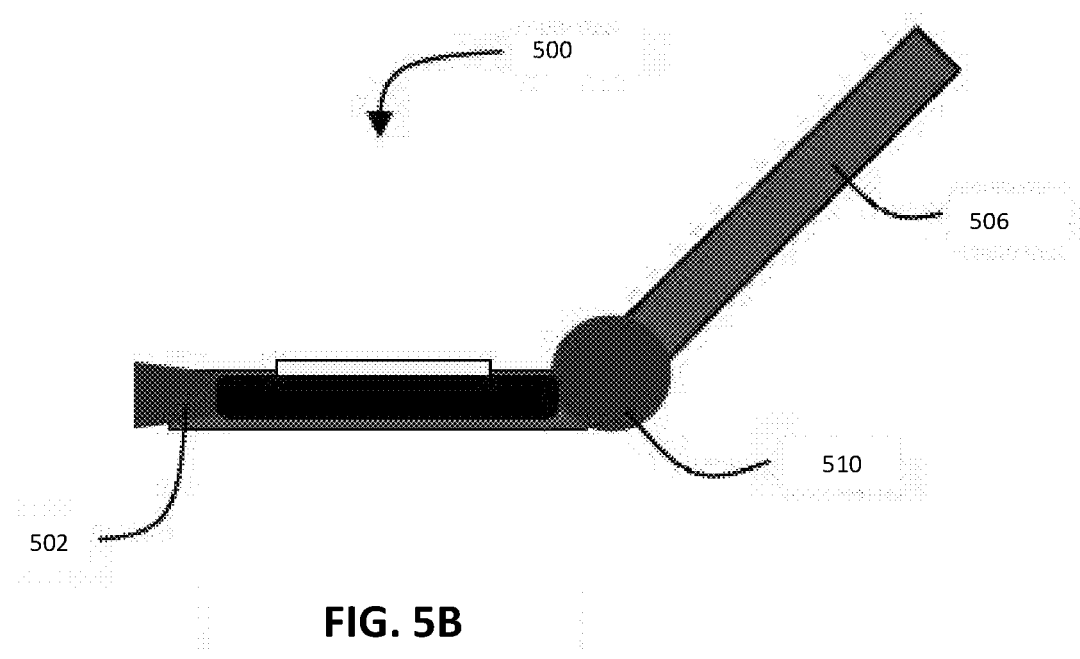
FIG. 5B-5F are schematic side views of examples of sample holders in accordance with some example implementations.
Figure 5C:
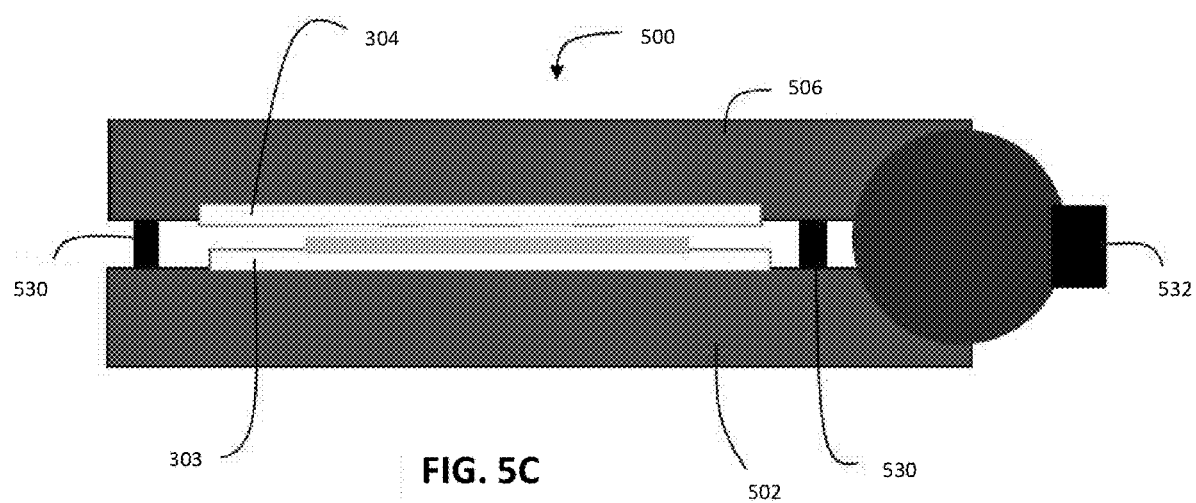

FIG. 5A is a schematic top view of an example of a sample holder 500, and FIGS. 5B and 5C are schematic side view of sample holder 500. Sample holder 500 includes a first member 502 that includes a first retaining mechanism 504 that retains substrate 303 with sample 302. Sample holder 500 also includes a second member 506 that includes a second retaining mechanism 508 that retains second substrate 304 with feature array 306. An alignment mechanism 510 is connected to at least one of first and second members 502 and 506 (to both first and second members 502 and 506 in FIGS. 5A and 5B). During an alignment and contacting procedure, alignment mechanism 510 functions to align the first and second members 502 and 506, thereby ensuring that sample 302 and feature array 306 are also aligned and brought into contact to facilitate analysis of sample 302.

As shown in FIGS. 5A-5C, in some embodiments, alignment mechanism 510 can be implemented as a rotating actuator connected to the first and second members 502 and 506. The alignment mechanism 510 may be implemented as a locating pin and/or a locating tab connected to the first and second members 502 and 506. One example of a rotating actuator is a hinge. As shown in FIG. 5B, once a substrate-mounted sample 303 is positioned in the first member 502 and a substrate-mounted feature array 304 is positioned in the second member 506, rotation of one of the members about the hinge axis aligns members 502 and 506, and also aligns sample 302 and feature array 306. The members can be rotated about the hinge axis until, as shown in FIG. 5C, sample 302 and feature array 306 are aligned and in contact.

Figure 5D:
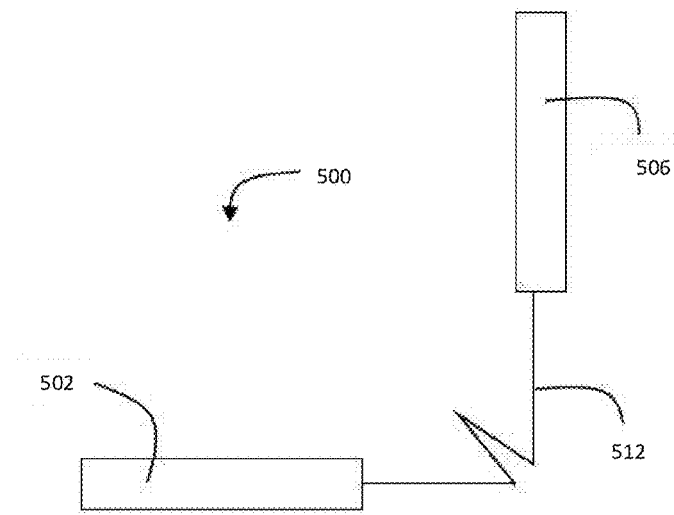

While the rotating actuator can be implemented as a hinge in some embodiments as shown in FIGS. 5A-5C, other implementations are also possible. For example, in certain embodiments, the rotating actuator is implemented as a folding member. FIG. 5D shows a schematic side view of an example sample holder 500 that includes a folding member 512 connected to first and second members 502 and 506. Folding member 512 functions in a manner similar to the hinge described above, aligning members 502 and 506, and sample 302 and feature array 306. Folding member can be formed from a variety of materials, including compliant materials such as rubber and vinyl, metals and metal alloys, and plastics.

Figure 5E:
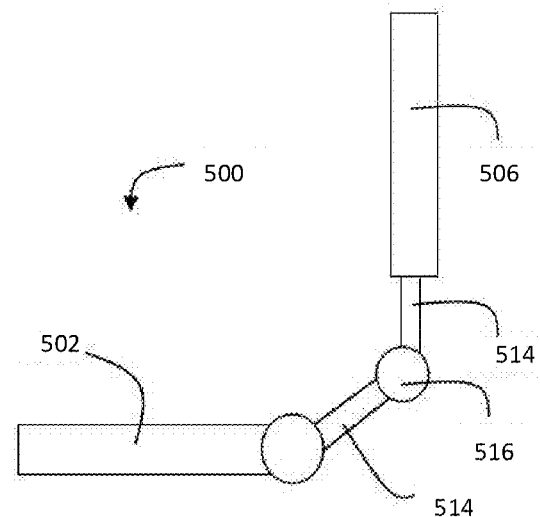

In certain embodiments, rotating actuator 510 can include at least one arm. FIG. 5E shows a schematic side view of an example sample holder 500 that includes a rotating actuator implemented as an arm 514 connected to first and second members 502 and 506. Arm 514 includes an internal pivoting mechanism 516 (e.g., a pin) that allows arm 514 to fold, bringing members 502 and 506 into alignment, thereby aligning sample 302 and feature array 306. Although only one arm 514 is shown in FIG. 5E, more generally rotating actuator 510 can include multiple arms (e.g., 2 or more, 3 or more, 4 or more, or even more).

Figure 5F:
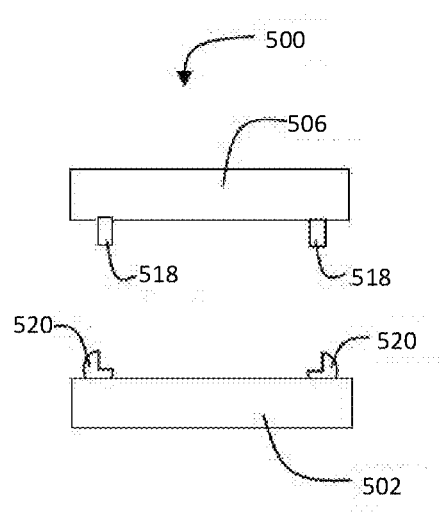

In each of the examples of sample holder 500 discussed above, sample holder 500 is implemented as a unitary (i.e., one-piece) device. Sample holder 500 can also be implemented as a two-piece device, with first and second members 502 and 506 being separate but reproducibly connectable via alignment mechanism 510. FIG. 5F shows a schematic side view of an example of a two-piece sample holder 500. The alignment mechanism can be implemented in various ways. In FIG. 5F, the alignment mechanism consists of connectors 518 positioned on second member 506 and receivers 520 positioned on first member 502. When the first and second members 502 and 506 are brought into proximity, connectors 518 engage with receivers 520, aligning first and second members 502 and 506, and also aligning sample 302 with feature array 306. It should be noted that while connectors 518 are positioned on second member 506 and receivers 520 are positioned on first member 502 in FIG. 5F, the reverse could also be true. Moreover, first and second members 502 and 506 could each have one or more connectors 518 and one or more receivers 520.

The first retaining mechanism 504 can be implemented in various ways. In some embodiments, first retaining mechanism 504 can correspond to a recess dimensioned to receive first substrate 303. Further, a gasket can optionally be positioned within the recess to maintain an interference fit between the edges of the recess and first substrate 303.

In certain embodiments, first retaining mechanism 504 can correspond to one or more members positioned to apply a force to first substrate 303, in particular, to maintain contact between first substrate 303 and first member 502. Examples of such members include, but are not limited to, clips, screws and other threaded retaining fasteners, and members that snap-fasten or otherwise engage with first member 502. The members can apply a force to the sample bearing surface of first substrate 303 and/or to one or more lateral surfaces first substrate 303.

In general, second retaining mechanism 508 can correspond to any of the different types of retaining mechanisms discussed above in connection with first retaining mechanism 504. First and second retaining mechanisms 504 and 508 can be different or the same.

In some embodiments, the first member 502 includes a first aperture 522. The first aperture 522 can be positioned, for example, so that when the first substrate 303 is retained in first member 502, first aperture 522 is aligned with a sample region (e.g., a region where sample 302 is typically located, or which is designated for placement of sample 302) on first substrate 303. Aperture 522 can be positioned so that sample 302 can be viewed from the back surface of first member 502 (e.g . . . , the surface opposite to the surface that supports first substrate 303) through first aperture 522, and one or more images of sample 302 can be obtained through first aperture 522.

As described above, a feature array 306 can be positioned on second substrate 304. More generally, however, second substrate 304 supports a reagent medium that is used to analyze sample 302. In some embodiments, the reagent medium corresponds to feature array 306. In certain embodiments, the reagent medium includes feature array 306 and one or more additional components. For example, the additional components can include a permeabilization reagent (e.g., a solid, liquid, gel, or dried permeabilization reagent). As an additional example, the additional components can include a hydrogel compound or layer with an embedded permeabilization reagent.

Figure 6:
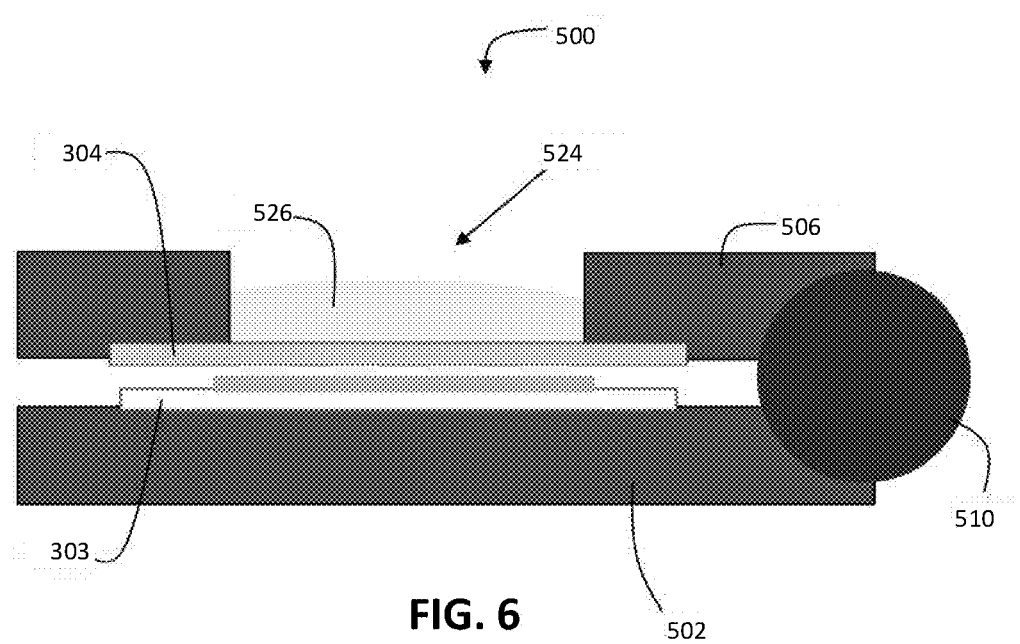
FIG. 6 is a schematic side view of an example of a sample holder in accordance with some example implementations.

In some embodiments, second member 506 includes at least one aperture. FIG. 6 shows a schematic side view of an example of a sample holder 500 in which second member 506 includes an aperture 524. More generally, second member 506 can include one or more (e.g., 2 or more, 3 or more, 4 or more, 5 or more, 6 or more, 8 or more, 10 or more, 15 or more, 20 or more, 30 or more, 40 or more, 50 or more, or even more) second apertures 524. In certain embodiments, second aperture 524 is aligned with at least a portion of the sample region on substrate 303 and/or the first aperture(s) 522 when first and second members 502 and 506 are aligned.

Second aperture 524 can used for various purposes. In some embodiments, for example, feature array 306 and/or sample 302 can be viewed or imaged through second aperture 524. Viewing/imaging can be used to adjust the relative positions of feature array 306 and sample 302 to improve alignment, for example.

In certain embodiments, one or more bounding surfaces of second aperture 524 and a back surface of second substrate 304 (i.e., a surface of second substrate 304 that is opposite to the surface of second substrate 304 that faces sample 302 and that supports feature array 306) cooperate to form a reagent well. A reagent solution 526 (e.g., comprising a permeabilization reagent) added to the reagent well is contained by the bounding surfaces of second aperture 524. If second substrate 304 is formed from a permeable or semi-permeable material, the reagent solution 526 can permeate (e.g., by diffusion) through the back surface of second substrate 304 and contact sample 302.

In some embodiments, sample holder 500 includes a first adjustment mechanism 528 connected to first member 500. First adjustment mechanism 528 translates first substrate 303 in at least one direction parallel to the surface of first substrate 303 that supports sample 302. In some embodiments, first adjustment mechanism 528 translates first substrate 303 in two directions parallel to the surface of first substrate 303.

First adjustment mechanism 528 can be implemented in various ways. In some embodiments, for example, first adjustment mechanism 528 includes one or more thumbscrews (e.g., as shown in FIG. 5A) or linear actuators that can be used to translate first substrate 303.

In addition to aligning first and second members 502 and 506, alignment mechanism 510 may also be configured to maintain a separation between first and second substrates 303 and 304 (and first and second members 502 and 506) when the substrates (and members) are aligned. For example, the separation can be maintained such that at least a portion of sample 302 contacts the reagent medium (e.g., feature array 306 of the reagent medium).

The separation between first and second substrates 303 and 304 can be maintained between 50 microns and 1 mm (e.g., between 50 microns and 800 microns, between 50 microns and 700 microns, between 50 microns and 600 microns, between 50 microns and 500 microns, between 50 microns and 400 microns, between 50 microns and 300 microns, between 50 microns and 200 microns, between 50 microns and 100 microns), measured in a direction orthogonal to the surface of first substrate 303 that supports sample 302.

In certain embodiments, alignment mechanism 510 maintains first and second substrates 303 and 304 in an approximately parallel relationship when the substrates (and first and second members 502 and 506) are aligned. An included angle between first and second substrates 303 and 304 in such circumstances can be 2 degrees or less (e.g., 1 degree or less, 0.5 degrees or less, 0.25 degrees or less).

In some embodiments, sample holder 500 can include one or more spacing members 530 that assist in maintaining the spacing and/or approximately parallel arrangement of first and second substrates 303 and 304. Examples of such spacing members 530 are shown in FIG. 52C. Spacing members 530 can be connected to either or both of first and second members 502 and 506.

In certain embodiments, sample holder 500 includes a second adjustment mechanism 532, as shown in FIG. 5C. Second adjustment mechanism 532 adjusts a distance of the separation between first and second substrates 303 and 304 (i.e., in a direction orthogonal to the surface of first substrate 303 that supports sample 302). As shown in FIG. 5C, in some embodiments, second adjustment mechanism 532 is connected to at least one of first member 502 and second member 506; in certain embodiments, adjustment mechanism 532 is connected to both members 502 and 506. The second adjustment mechanism 532 can be a component of adjustment mechanism 510, or alternatively, can be implemented as a separate component as in FIG. 5C.

Second adjustment mechanism 532 can be implemented in various ways. In some embodiments, second adjustment mechanism 532 includes one or more thumbscrews or adjustable pins or posts. In certain embodiments, second adjustment mechanism 532 includes one or more linear actuators. In some embodiments, second adjustment mechanism 532 includes a swellable or expandable membrane, gasket, or layer positioned between first and second members 502 and 506.

As a subsequent step in an analytical workflow, after sample 302 and feature array 306 have been brought into contact by sample holder 500, sample holder 500 can be introduced into a thermocycler to promote capture of analytes from sample 302 by feature array 306. Sample holder 500 can be inserted directly into a suitable thermocycler for this purpose. Alternatively, in some embodiments, sample holder 500 can be coupled to a thermocycler adapter and the coupled holder and adapter inserted into a thermocycler. Suitable thermocycler adapters for use with sample holder 500 are described, for example, in U.S. Provisional Patent Application No. 62/839,575, filed on Apr. 26, 2019, the entire contents of which are incorporated herein by reference.

Sample holder 500 is compatible with a variety of different schemes for contacting sample 302 with a permeabilization reagent to promote analyte capture. In some embodiments, a permeabilization reagent solution is deposited directly on second substrate 304 (e.g., forming a reagent medium that includes the permeabilization reagent and feature array 306), and/or directly on first substrate 303, and then sample 302 is contacted to the feature array 306 (e.g., by closing sample holder 500 as shown in FIG. 5C).

In certain embodiments a dried permeabilization reagent is applied or formed as a layer on first substrate 303 or the second substrate 304 or both prior to contacting sample 302 and feature array 306. For example, a reagent can be deposited in solution on first substrate 303 or second substrate 304 or both and then dried. Drying methods include, but are not limited to spin coating a thin solution of the reagent and then evaporating a solvent included in the reagent or the reagent itself. Alternatively, in other embodiments, the reagent can be applied applied in dried form directly onto the first substrate 303 or second substrate 304 or both. In some embodiments, the coating process can be done in advance of the analytical workflow and the first substrate 303 and second substrate 304 can be stored precoated. Alternatively, the coating process can be done as part of the analytical workflow. In some embodiments, the reagent is a permeabilization reagent. In some embodiments, the reagent is a permeabilization enzyme, a buffer, a detergent, or any combination thereof. In some embodiments, the permeabilization enzyme is pepsin. In some embodiments, the reagent is a dried reagent (e.g., a reagent free from moisture or liquid).

The first substrate 303, which includes a feature array 306, may be contacted with the dried permeabilization reagent 526. In some embodiments, the first substrate 303 is contacted with a permeabilization reagent that is a gel or a liquid. The sample 302 may be contacted with a buffer. Both first and second substrates 303 and 304 may be placed at lower temperature to slow down diffusion and permeabilization efficiency. Alternatively, in some embodiments, the sample 302 can be contacted directly with a liquid permeabilization reagent without inducing an unwanted initiation of permeabilization due to the substrates being at the second temperature. In some embodiments, the low temperature slows down or prevents the initiation of permeabilization.

The sample holder 500 (and consequently the first and second substrates 303 and 304) may be heated up to initiate or increase permeabilization. In some embodiments, the sample holder 500 is heated up to a third temperature. In some embodiments, the third temperature is above room temperature (e.g., 25 degrees Celsius) (e.g., 30 degrees Celsius or higher, 35 degrees Celsius or higher, 40 degrees Celsius or higher, 50 degrees Celsius or higher, 60 degrees Celsius or higher). In some embodiments, analytes that are released from the permeabilized tissue of sample 302 diffuse to the surface of the first substrate 303 and are captured on the feature array 306 (e.g., barcoded probes) of the second substrate 304. After heating, the first substrate 303 and the second substrate 304 may be separated (e.g., pulled apart) and temperature control may be stopped.

In some embodiments, where either first substrate 303 or substrate second 304 (or both) includes wells, a permeabilization solution can be introduced into some or all of the wells, and then sample 302 and feature array 306 can be contacted by closing sample holder 500 to permeabilize sample 302. In certain embodiments, a permeabilization solution can be soaked into a hydrogel film that is applied directly to sample 302, and/or soaked into features (e.g., beads) that form feature array 306. When sample 302 and feature array 306 are contacted by closing sample holder 500, the permeabilization solution promotes migration of analytes from sample 302 to feature array 306.

In certain embodiments, different permeabilization agents or different concentrations of permeabilization agents can be infused into array features (e.g., beads) or into a hydrogel layer as described above. By locally varying the nature of the permeabilization reagent(s), the process of analyte capture from sample 302 can be spatially adjusted.

It should also be noted that in connection with any of the above permeabilization methods, in some embodiments, migration of the permeabilization agent into sample 302 can be passive (e.g., via diffusion). Alternatively, in certain embodiments, migration of the permeabilization agent into sample 302 can be performed actively (e.g., electrophoretic, by applying an electric field to promote migration).

In the foregoing description of sample holder 500, assembly or closing of sample holder 500 as shown in FIG. 5C can be performed manually. Alternatively, in some embodiments, sample holder 500 can be closed using one or more motorized actuators (e.g., as alignment mechanism 510), controlled by a dedicated controller or by software running on a specialized or general purpose computing device that includes one or more electronic processors, application-specific integrated circuits, and/or dedicated programmable controllers.

Although first and second substrates 303 and 304 are shown in FIG. 5A as being of the same dimensions, more generally, first and second members 502 and 506 can accommodate first and second substrates 303 and 304 of different sizes and/or shapes. In certain embodiments, the first and/or second retaining mechanisms 504 and 508 are shaped to accommodate specific sizes and/or shapes of first and second substrates 303 and 304. In certain embodiments, the first and/or second retaining mechanisms 504 and 508 are adjustable, and can accommodate substrates having different sizes and/or shapes.

In some embodiments, where first and second substrates 303 and 304 are longer in one transverse direction than in the other transverse direction as shown in FIG. 5A, sample holder 500 can be configured to receive first and second substrates 303 and 304 such that when sample holder 500 is closed, the longer dimensions of the substrates are aligned orthogonally. Because first adjustment mechanism 528 permits translation of first substrate 303 parallel to direction, sample 302 can be positioned at nearly any location on substrate 303 and still aligned (by adjusting first adjustment mechanism 528) with feature array 306.

To ensure that sample 302 and feature array 306 are brought into alignment by sample holder 500, in some embodiments fiducial markings on first substrate 303 and/or second substrate 5106 can be viewed or imaged (e.g., through first aperture 522 and/or second aperture 524, and first adjustment mechanism 528 can be adjusted so that the fiducial marks are aligned with one another. Alignment between first and second substrates 303 and 304 can also be adjusted even when first and second substrates 303 and 304 do not include fiducial markings.

EXAMPLES

Example 1

To evaluate different permeabilization schemes using sample holder 500, a series of experiments were conducted. In a first experiment, a permeabilization solution was applied to the surface of second substrate 304, and first and second substrates 303 and 304 were aligned such that sample 302 contacted feature array 306, and the permeabilization solution diffused into sample 302, promoting the release of analytes from sample 302. The analytes were captured by array 306. A total of 20 µL of 4× permeabilization solution was used, and permeabilization and analyte migration were carried out for 6 minutes at 37° C.

Figure 7:
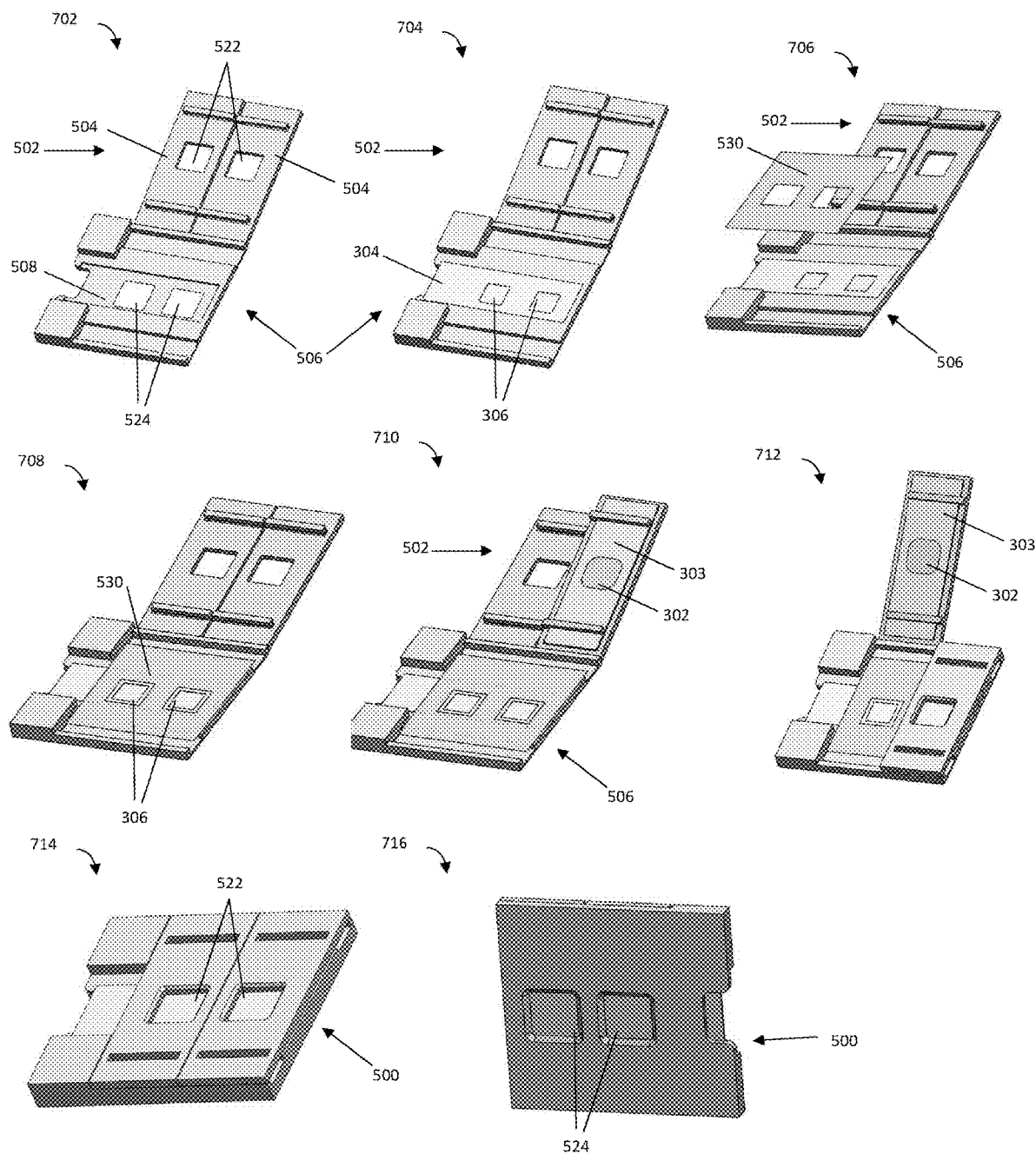
FIG. 7 shows an example analytical workflow using an example sample holder in accordance with some example implementations.

FIG. 7 shows an example analytical workflow using the example sample holder 500. At a first step 702, an empty sample holder 500 is placed in an open position. The open position may allow a user to more easily add or remove slides (e.g., substrates) to/from the sample holder 500. As shown in the example of FIG. 7, the sample holder 500 includes two first retaining mechanisms 504, the first member 502 includes two first apertures 522, and the second member 506 includes two second apertures 524.

At step 704, a second substrate 304 may be loaded into the second member 506, also referred to as a base member (e.g., via the second retaining mechanism 508). As shown, the second substrate 304 includes two feature arrays 306. The feature arrays 306 may be positioned over the second a pictures 524 when the second substrate 304 is aligned within the second member 506.

At step 706, a spacing member 530 may be positioned within the sample holder 500. At step 708, the spacing member 530 is positioned in an example location within the sample holder 500. As shown in step 708, the spacing member 530 is placed over the second substrate 304 within the second member 506. As further shown, the spacing member 530 includes apertures sized and shaped to fit over the feature arrays 306 of the second substrate 304. In some aspects, the spacing member 530 and/or the second member 506 may include an adhesive (e.g., a pressure sensitive adhesive (PSA), glue, VELCRO® hook-and-loop fasteners, tape, or the like) configured to couple the spacing member 530 to the second member 506 and retain the spacing member 530 in a desired position.

At step 710, a first substrate 303 may be loaded into the first member 502 (e.g., via a first retaining mechanism 504). As shown, the first substrate 303 may include the sample 302. At step 712, a second first substrate 303 may be loaded into the first member 502 (e.g., via a second first retaining mechanism 504). As shown, the second first substrate 303 includes a second sample 302. In some aspects, upon closing the first member 502 over the second member 506, the samples 302 may be aligned with and/or may contact the feature arrays 306.

At step 714, a user may add a reagent solution (e.g., permeabilization solution 305) to the first substrate 303 and/or the second substrate 304. In some aspects, the user may add reagent solution to a location proximate or above the feature arrays 306. In some embodiments, the sample holder apparatus may be configured to add the reagent solution. After adding the reagent solution, the user may close the first member 502 over the second member 506. Alternatively, in some embodiments, sample holder 500 can be closed using one or more motorized actuators (e.g., as alignment mechanism 510), controlled by a dedicated controller or by software running on a specialized or general purpose computing device that includes one or more electronic processors, application-specific integrated circuits, and/or dedicated programmable controllers. As shown in step 714, the closed sample holder 500 includes first apertures 522 of the first member 502. After closing the first member 502 over the second member 506, the permeabilization solution 305 may contact the one or more samples 302 and promote release of analytes from the one or more samples 302 to the feature arrays 306 of the second substrate 304.

At step 716, the closed sample holder 500 includes second apertures 524 of the second member 506. The closed sample holder 500 may then be transferred to a different apparatus or location for imaging, heating, analysis, or the like.

Figure 8:
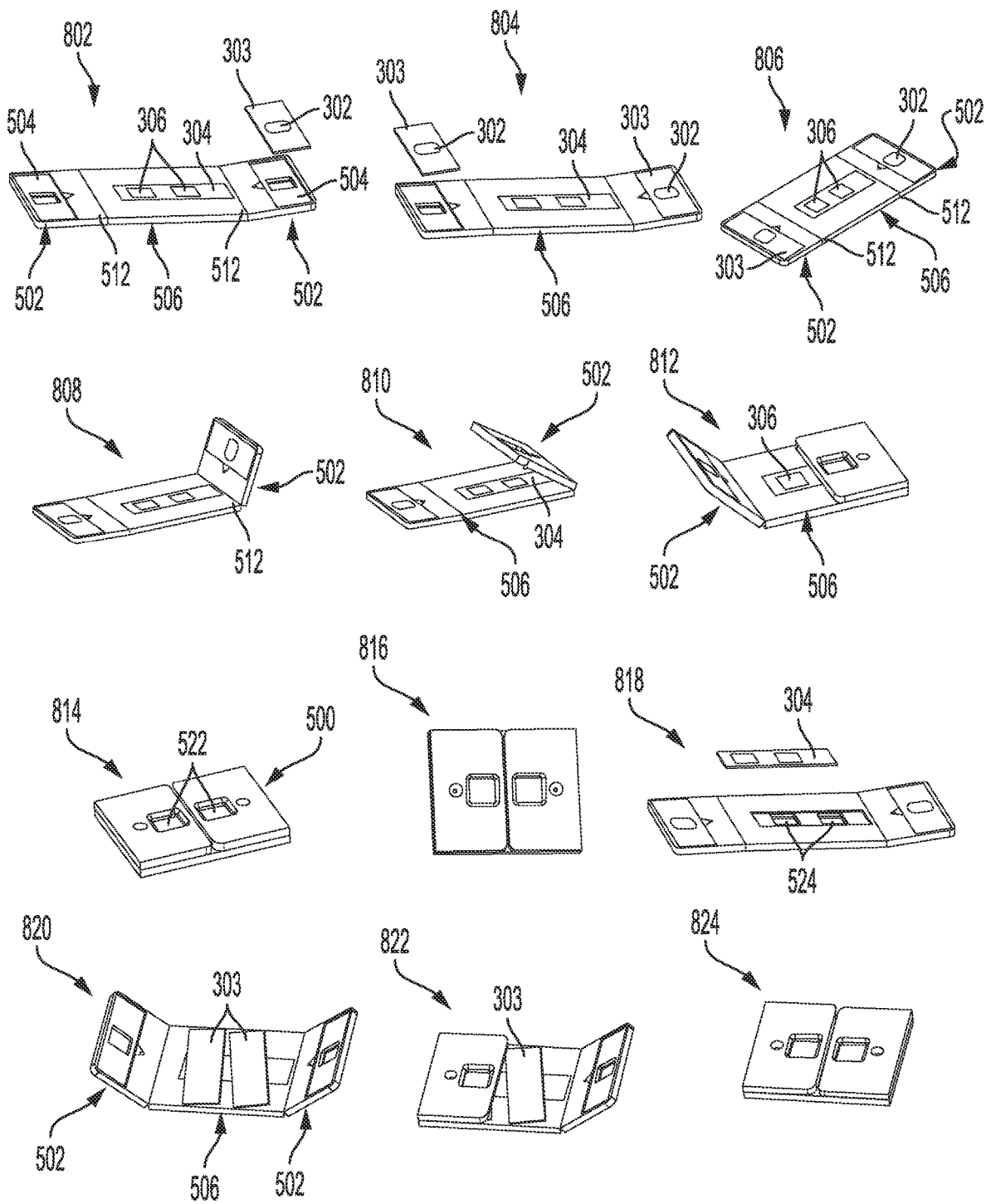
FIG. 8 shows an example analytical workflow using an example sample holder having folding members in accordance with some example implementations.

FIG. 8 shows an example analytical workflow using the example sample holder 500 having folding members 512. At step 802, the sample holder 500 is in an open position with a second substrate 304 located within the second member 506. As further shown, the sample holder 500 includes two first members 502 and a second member 506. The example sample holder 500 of FIG. 8 includes folding members 512 couple to the second member 506 and the first members 502. The second substrate includes two feature arrays 306. As further shown, a first substrate 303 having a first sample 302 is loaded into a first member 502 (e.g., via a first retaining mechanism 504 located at right-hand side of the sample holder 500 shown at step 802).

At step 804, a second first substrate 303 having a second sample 302 is loaded into a first member 502 (e.g., via a second first retaining mechanism 504 located at left side of the sample holder 500 shown at step 804).

At step 806, the sample holder 500 is configured in an open position with first substrates 303 located within the first members 502 and with the second substrate 304 positioned within the second member 506.

At step 808, the first member 502 (e.g., at the right hand side of sample holder 500) begins closing over the second member 506 via the folding member 512. At step 810, the first member 502 further closes over the second member 506. At step 812, the right-hand first member 502 is closed over the second member 506. As shown, folding the first member 502 over the second member 506 may align the first sample 302 over a feature array 306 of the second substrate 304. As further shown in step 812, the left-hand first member 502 begins closing over the second member 506.

At step 814, the left-hand first member 502 is closed over the second member 506 and the second sample 302 of the left-hand first member 502 may be aligned with the remaining feature array 306 of the second substrate 304.

At step 816, the closed sample holder 500 may then be transferred to a different apparatus or location for imaging, heating, analysis, or the like.

At step 818, the sample holder 500 may be opened and the second substrate 304 may be removed to perform spatial analysis, reverse transcription, or the like.

At step 820, the first substrates 303 may be removed from the first members 502. In some aspects, the first substrates 303 and/or the second substrate 304 may be replaced to perform additional analysis.

At step 822, the sample holder 500 is partially closed with a first substrate 303 disposed within the left-hand first member 502 and a second first substrate 303 positioned external to the first members 502 and positioned over the second substrate 304.

At step 824, the closed sample holder 500 may then be transferred to a different apparatus or location for imaging, heating, analysis, or the like.

Figure 9:
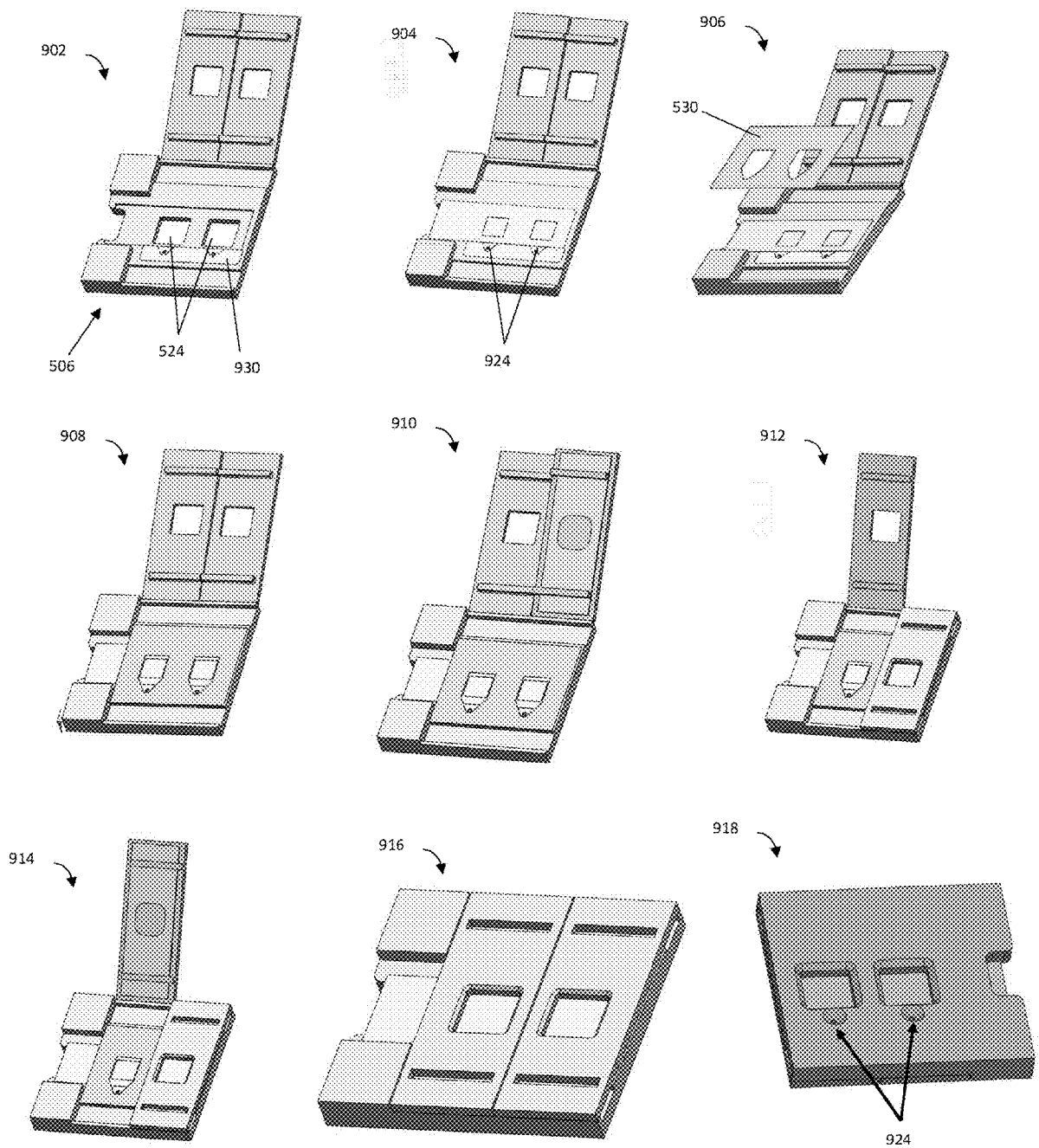
FIG. 9 shows an example analytical workflow using an example sample holder forming a flow cell in accordance with some example implementations.

FIG. 9 shows an example analytical workflow using the example sample holder 500 forming a flow cell. FIG. 9 is similar to an adapted from the example workflow of FIG. 7. At least some of the differences between FIGS. 7 and 9 are described herein for the sake of brevity.

At step 902, sample holder 500 is displayed in an open configuration. The second member 506 includes a recess portion that dimensioned to receive the second substrate 304. As shown, the recess portion includes a gasket 930. The gasket 930 may include a silicone gasket configured to contact the second substrate 304 and create a seal with the second substrate. Such a seal may facilitate the flow cell configuration and allow the permeabilization solution 305 to diffuse toward the feature arrays 306 and/or the sample(s) 302.

At step 904, the second substrate 304 is loaded into the second member 506 (e.g., within the recess portion). As shown, the gasket 930 may be positioned within the recess portion and over reagent wells 924. The reagent wells 924 may be configured to retain a volume of the permeabilization solution 305 such that when the first member 502 closes over the second member 506, the permeabilization solution 305 diffuses toward the feature arrays 306 and/or the sample(s) 302 within the sample holder 500.

At step 906, a spacing member 530 may be positioned within the sample holder 500. As shown, the spacing member 530 is sized and shaped to mate with the feature arrays 306 and the reagent wells 924.

At steps 908-914, the spacing member 530 is secured in place and first substrates 303 having samples 302 are loaded into the sample holder 500.

At step 916, the first member 502 (e.g., lid of the sample holder 500) is closed over the second member 506. The closing may form a sandwich configuration for the first substrates 303 and the second substrate 304. The closing may also form a flow cell. Forming a flow cell may include forming a chamber (e.g. a volume defined by the first substrate 303, the second substrate 304, the spacing member 530, or the like) in which it is possible to insert and/or remove a fluid (e.g., a reagent solution such as the permeabilization solution 305). In some aspects, after the closing step 916, the sample holder 500 may be transferred to a different apparatus or location for imaging, heating, analysis, or the like.

At step 918, the user may flip the sample holder 500 over and may load a reagent solution (e.g., permeabilization solution 305) through the ports 925 positioned proximate to the second apertures 524 on a back surface of the second member 506. In some aspects, the ports 925 may include a one-way valve and may allow injection of a defined volume of fluid (e.g., via pipetting, syringe, capillary flow, or the like) into the flow cell to facilitate permeabilization and analyte release. Using the ports 925 rather than placing a droplet directly on the first substrate 303 and/or the second substrate 304 (e.g., as described with respect to step 714), may beneficially reduce or eliminate bubble formation in the reagent solution during permeabilization. In some implementations, after adding the reagent solution, the sample holder 500 may be transferred to a different apparatus or location for imaging, heating, analysis, or the like.

Figure 10A:
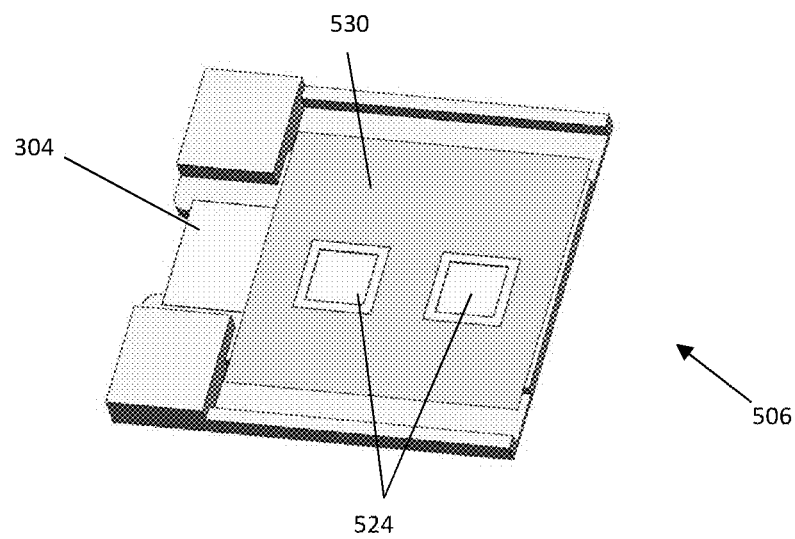
FIG. 10A depicts an example second member preloaded with a second substrate and a spacing member in accordance with some example implementations.

FIG. 10A depicts an example second member 506 preloaded with a second substrate 304, and a spacing member 530. In some aspects, the spacing member 530 may be preassembled and coupled to the second member 506 and/or the second substrate 304 using a variety of coupling means. For example, the spacing member 530 and/or the second member 506 may include an adhesive to secure and maintain a connection between the spacing member 530 and the second member 506. The adhesive may include a pressure sensitive adhesive (PSA), a glue, a tape, magnets, mechanical connectors, or the like.

Figure 10B:
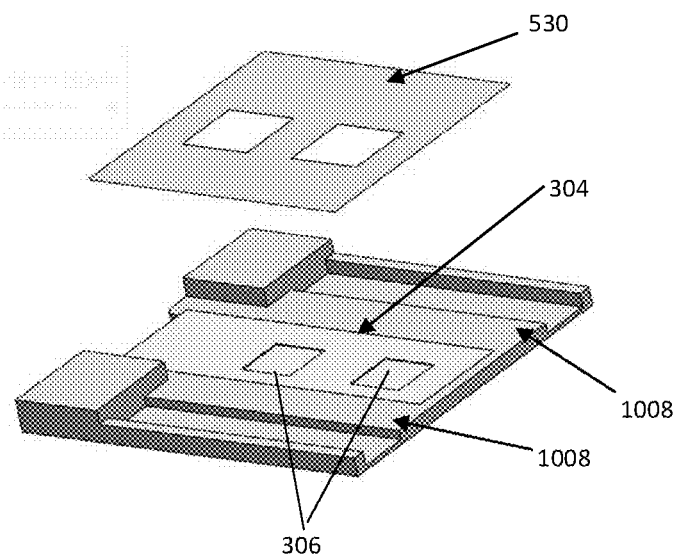
FIG. 10B depicts an exploded view of the second member, the second substrate, and the spacing member of FIG. 10A in accordance with some example implementations.

FIG. 10B depicts an exploded view of the second member 506, the second substrate 304, and the spacing member 530 of FIG. 10A. As shown in the example of FIG. 10B, locations 1008 may include the adhesive on the second member 506 which may couple to the spacing member 530. In some aspects, the spacing member 530 may include a removable backing (e.g., a plastic backing) on a side of the spacing member 530 contacting the second member 506 and/or the second substrate 304. The removable backing may protect an adhesive disposed on the spacing member 530 prior to securing the spacing member to the second member 506 and/or the second substrate 304.

Figure 11A:
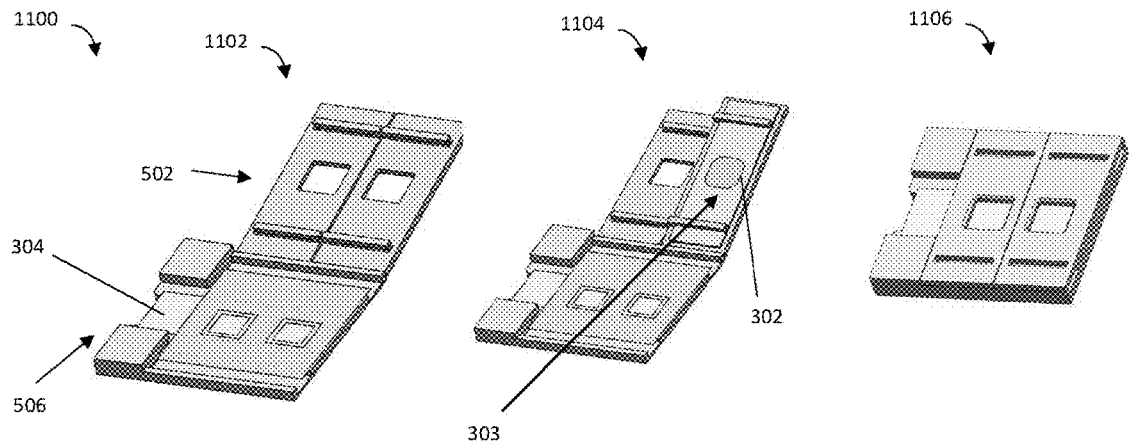
FIGS. 11A, 11B depict example workflows for loading first substrate(s) into an example sample holder.

FIG. 11A depicts an example workflow 1100 for loading a first substrate 303 into an example sample holder 500. At step 1102, the second member 506 is loaded with the second substrate 304 and the spacing member 530 and the first member 502 is empty. At step 1104, a first substrate 303 having a sample 302 is loaded into the first member 502 (e.g., via a first retaining mechanism 504). At step 1106, a reagent solution (e.g., permeabilization solution 305) may be added to the second substrate 304 and the first member 502 may be closed over the second member 506 to create a sandwich configuration (e.g., as shown in FIG. 3) and initialize the permeabilization step.

Figure 11B:
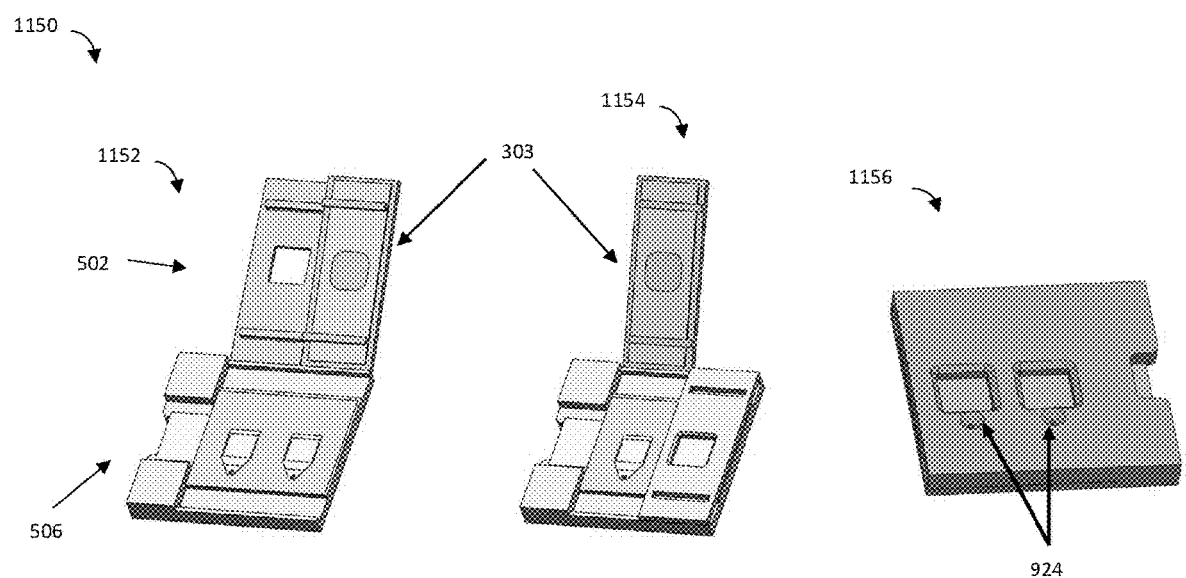

FIG. 11B depicts an example workflow 1150 for loading a first substrate 303 into an example sample holder 500. At step 1152, the second member 506 is loaded with the second substrate 304 and the spacing member 530 and the first member 502 is loaded with a first first substrate 303. As shown in FIG. 11B, the spacing member 530 is sized and shaped to at least partially surround the feature arrays 306 and the reagent wells 924. At step 1154, a second first substrate 303 is loaded into the first member 502 (e.g., via the first retaining mechanism 504). At step 1156, the first member 502 may close over the second member 506 to form a flow cell. In order to insert a reagent solution, the sample holder 500 may be flipped over to expose a back surface of the second member 506 and a user may insert the reagent solution through flow cell ports (e.g., reagent wells 924) in the back surface of the second member 506. the reagent solution (e.g., permeabilization solution 305) may diffuse toward the feature arrays 306 and/or the sample(s) 302 within the sample holder. In some aspects, the sample holder 500 may be transferred to another location or apparatus for imaging prior to inserting the reagent solution. Additionally or alternatively, the sample holder 500 may be transferred to another location or apparatus for heating, analysis, or imaging after inserting the reagent solution (e.g., via the reagent wells 924).

Figure 12A:
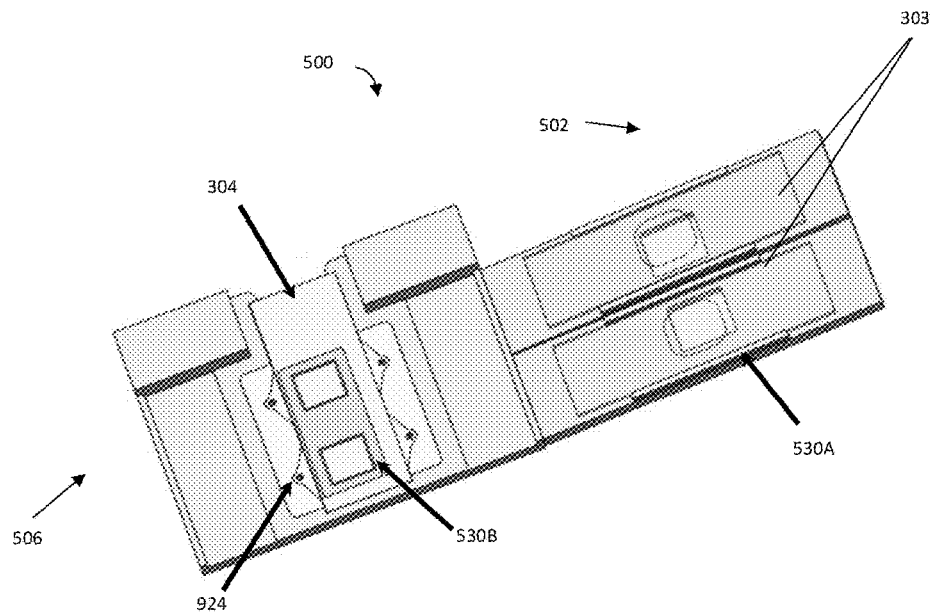
FIGS. 12A-12C show different views of the example sample holder in open and closed configurations in accordance with some example implementations.
Figure 12B:
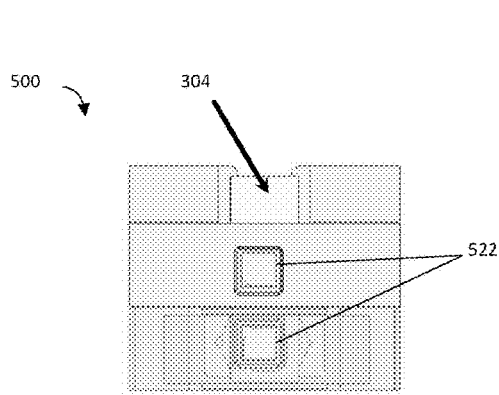
Figure 12C:
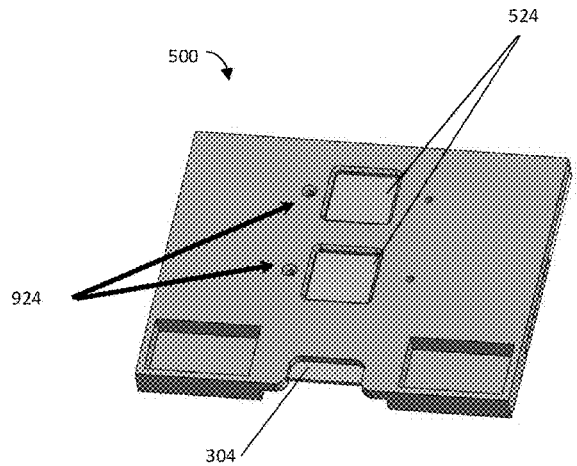

FIGS. 12A-12C show different views of an example sample holder 500 in open and closed configurations in accordance with some example implementations.

FIG. 12A shows a top view of the example sample holder 500 in an open configuration. As shown, a second substrate 304 having two feature arrays 306 is loaded into the second member 506 (e.g., via the second retaining mechanism 508) and two first substrates 303 are loaded into the first member 502 (e.g., via first retaining mechanisms 504). As further shown, the sample holder 500 includes a first spacing member 530A coupled to the first member 502 and a second spacing member 530B coupled to the second substrate 304. In some aspects, the second spacing member 530B may be additionally or alternatively coupled to the second member 506. The first spacing member 530A may have a thickness greater than the second spacing member 530B. For example, the first spacing member 530A may have a thickness of 50 μm and the second spacing member 530B may have a thickness of 12.5 μm. Although example thickness values are used herein for the first spacing member 530A and the second spacing member 530B, other values are possible. In some embodiments, the first substrate 303, the second substrate 304, the first spacing member 530A, and the second spacing member 530B may form a chamber (e.g., flow cell) when the first and second members 502 and 506 are aligned (e.g., when the first member 502 closes over the second member 506).

FIG. 12B is a top view of the example sample holder 500 of FIG. 12A in a closed position (e.g., the first member 502 is closed over the second member 506) in accordance with some example implementations. As shown, the first substrate 303 and/or the second substrate 304 may be viewed from the top via the first apertures 522.

FIG. 12C is a bottom view of the example sample holder 500 of FIG. 12A in a closed position (e.g., the first member 502 is closed over the second member 506) in accordance with some example implementations. As shown, the second substrate 304 and/or the first substrate 303 may be viewed from the bottom via the second apertures 524.

Figure 13A:
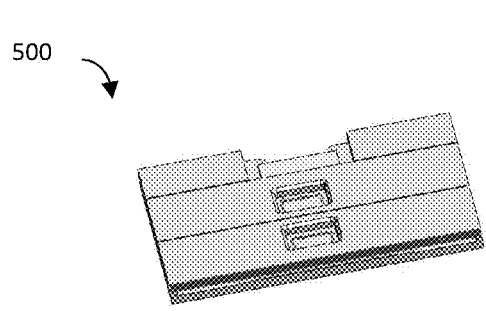
FIGS. 13A-13C show an example workflow of adding a reagent solution to an example sample holder in accordance with some example implementations.
Figure 13B:
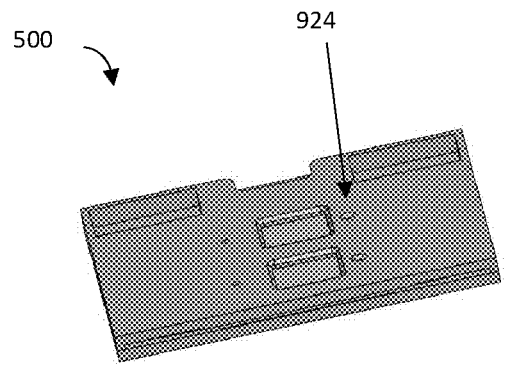
Figure 13C:
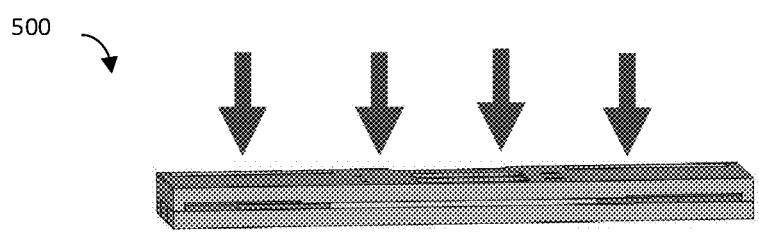

FIGS. 13A-13C show an example workflow of adding a reagent solution to an example sample holder 500 in accordance with some example implementations.

FIG. 13A is a perspective view of the sample holder 500 in a closed position. In the example of FIG. 13A, a first substrate 303 having a sample 302 has been loaded in the first member 502 and a second substrate 304 having an array 306 has been loaded in the second member 506. With reference to FIG. 12A, the sample holder 500 may include a first spacing member 530A and a second spacing member 530B having different thicknesses. For example, the first spacing member 530A may have a thickness of 50-200 μm and the second spacing member 530B may have a thickness of 12.5 μm. In some aspects, the first substrate 303, the second substrate 304, the first spacing member 530A, and the second spacing member 530B may form a chamber (e.g., flow cell) when the first and second members 502 and 506 are aligned (e.g., as shown in the example of FIG. 13A). A first height of the chamber may be defined by the first spacing member 530A (e.g., 200 μm).

FIG. 13B shows a perspective view of the example sample holder 500 flipped over and in the closed position. As shown, a reagent solution may be inserted in the reagent wells 924 (e.g., ports in the back surface of the second member 506).

FIG. 13C shows a side view of the example sample holder 500 in a closed position. As shown, the sample holder 500 may be compressed to a second height defined by the second spacing member 530B (e.g., 12.5 μm). In some aspects, compressing the sample holder may encourage or urge the reagent solution added via the reagent wells 924 toward the sample 302 and/or the feature array 306. In some implementations, after compressing the sample holder 500 to the second height, the sample holder 500 may be transferred to a different location or apparatus (e.g., a thermocycler) to heat the first and/or the second substrates 303, 304.

Figure 14A:
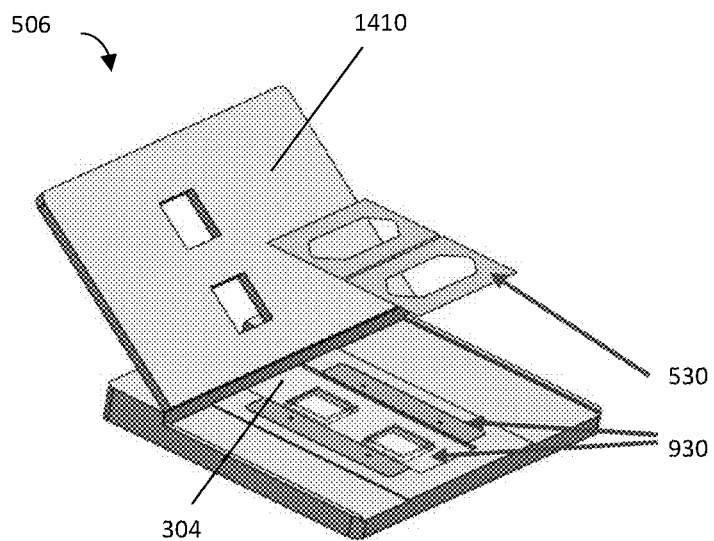
FIGS. 14A and 14B show bottom perspective views of an example second member having a lid in accordance with some example implementations.
Figure 14B:
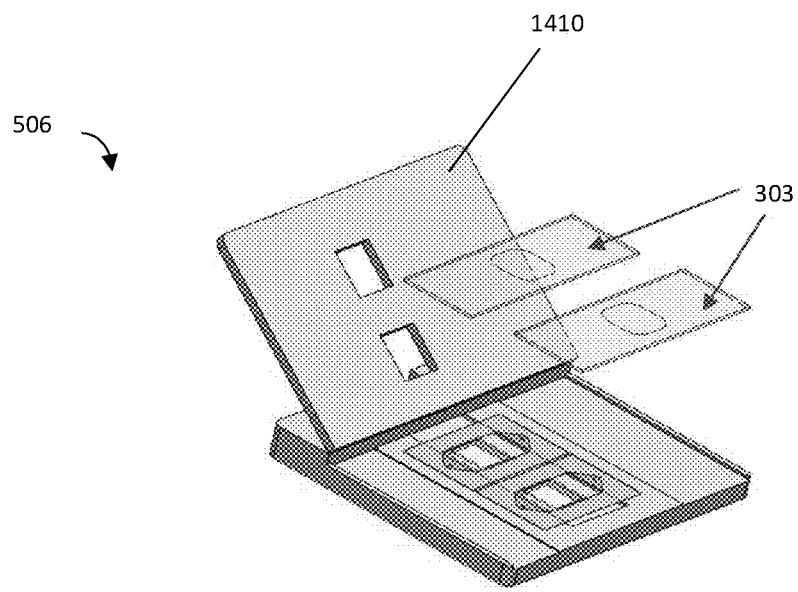

FIGS. 14A-14B show a bottom perspective view of an example second member 506 having a lid 1410 in accordance with some example implementations. FIG. 14A depicts the second member 506 having the lid 1410 in an open configuration. As shown, a second substrate (e.g., slide 304), gaskets 930 are loaded into the second member 506. In some aspects, the gaskets 930 may be installed in a recess of the second member 506. The gaskets 930 may be positioned over and may be in connection with ports (e.g., reagent wells 924) on the back surface of the second member 506. the gaskets 930 may up but and contact a side of the second substrate 304 such that the gaskets 930 create a seal between the gasket 930 and the second substrate 304. The seal may allow the reagent solution added via the ports (e.g., reagent wells 924) to migrate to the feature array 306 and/or the sample 302. As further shown, spacing member 530 may also be installed into the second member 506 (e.g., via the lid 1410). In some aspects, the second substrate 304, the gaskets 930, and/or the spacing member 530 may be preinstalled by the manufacturer in a factory and shipped to a customer (e.g., as a kit). The customer may then add or couple its own customer slides (e.g., slides 303) having corresponding sample(s) 302 to the second member 506 to perform spatial analysis (e.g., via the sandwich configuration described herein).

FIG. 14B makes a bottom perspective view of the example second member 506 with the lid 1410 in an open configuration. In the example of FIG. 14B, the second member 506 is preloaded with the second substrate 304 the gaskets 930, and the spacing member 530. As further shown, first substrates (e.g., slides 303) are loaded into the example second member 506. In some aspects, a customer may manually load the first substrates 303 into the second member 506. In some embodiments, the customer may load the entire preinstalled second member 506 into a sample holder apparatus (e.g., sample holder 500) to perform spatial analysis as described herein.

Figure 15A:
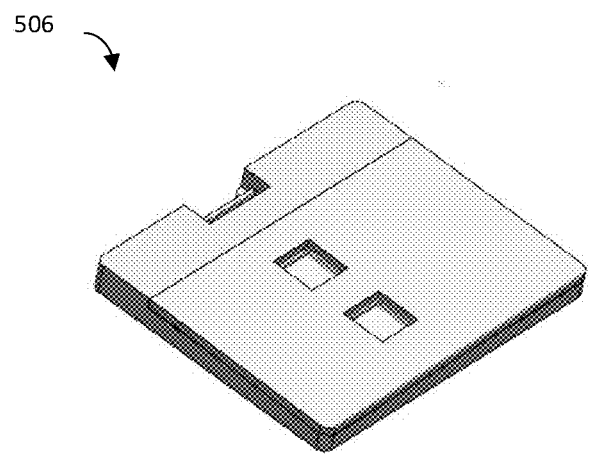
FIG. 15A depicts a perspective view of the second member of FIG. 14B with the lid in a closed configuration in accordance with some example implementations.

FIG. 15A depicts a perspective view of the second member 506 of FIG. 14B with the lid 1410 in a closed configuration. After closing the lid 1410, the second member 506 may be installed into a thermocycler to promote capture of analytes from sample 302 by feature array 306. Alternatively or additionally, the closed second member 506 of FIG. 15A may be installed or transferred to an image capture device to capture images of the sample(s) 302 and/or the feature arrays 306. Such image captures may occur prior to or after inserting a reagent solution (e.g., permeable is solution 305) into the second member 506.

Figure 15B:
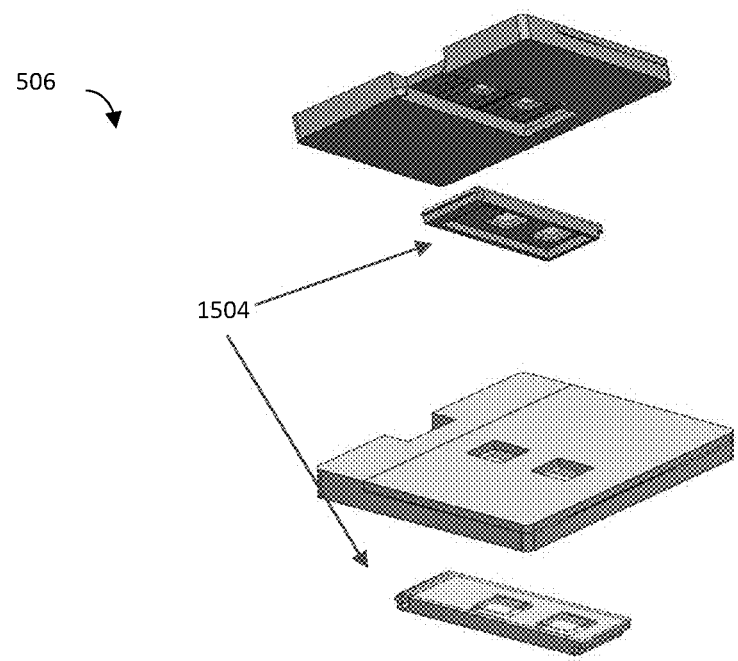
FIG. 15B depicts an exploded view of the second member having a removable portion in accordance with some example implementations.

FIG. 15B depicts an exploded view of the second member 506 having a removable portion 1504. As shown, the removable portion 1504 includes the second substrate 304. In some aspects the removable portion 1504 may include the gaskets 930, and/or the spacing member 530. In some implementations, the removable portion 1504 may be installed or transferred to another device to perform further analysis (e.g., reverse transcription, library sequencing, spatial analysis, or the like).

Figure 16:
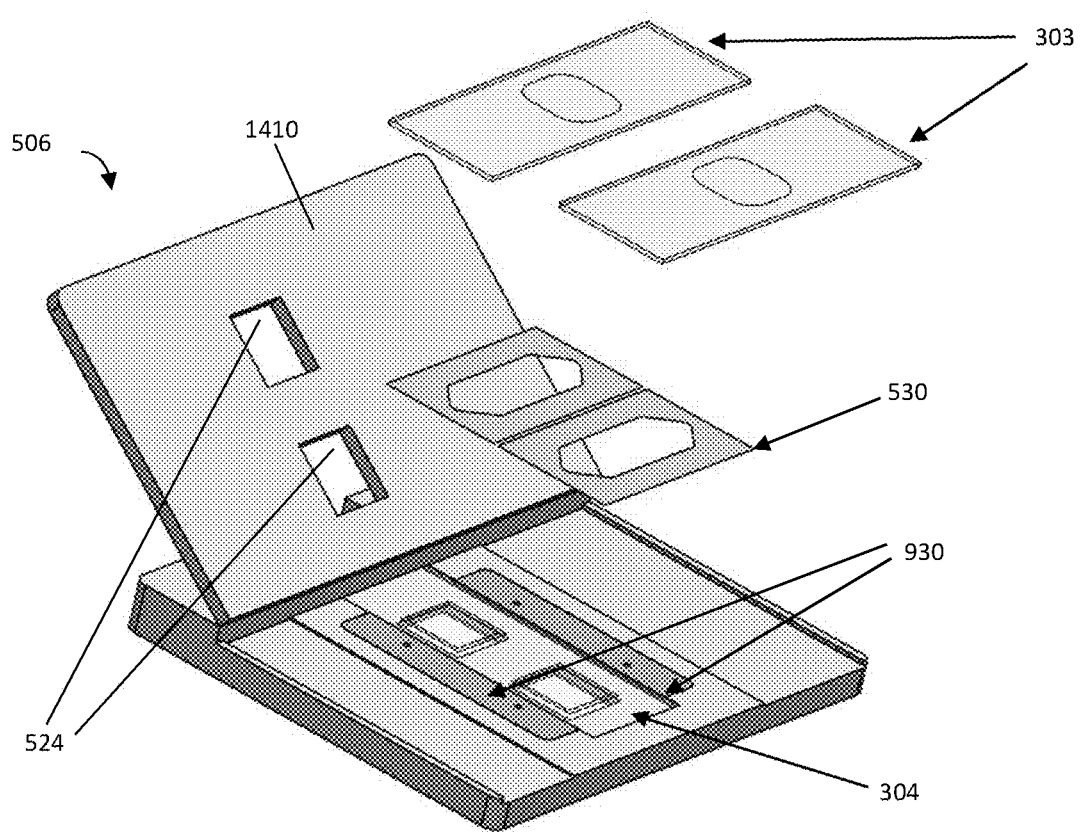
FIG. 16 depicts an exploded view of the second member having the lid in an open configuration in accordance with some example implementations.

FIG. 16 depicts an exploded view of the second member 506 having the lid 1410 in an open configuration. The example of FIG. 16 illustrates that second substrate 304 and the gaskets 930 may be preloaded into the second member 506. As shown, the spacing member 530 may be installed over the second substrate 304 within the second member 506. As further shown, one or more first substrates 303 may be installed into the second member 506 over the spacing member 530 and the sample(s) 302 of the one or more first substrates 303 may be aligned with the feature arrays 306 of the preinstalled second substrate 304.

OTHER EMBODIMENTS

It is to be understood that while the invention has been described in conjunction with the detailed description thereof, the foregoing description is intended to illustrate and not limit the scope of the invention, which is defined by the scope of the appended claims.

Disclosed are systems, apparatuses (e.g., devices), methods and compositions that can be used for, can be used in conjunction with, can be used in preparation for, or are products of the disclosed methods and compositions. These and other systems, apparatuses, methods and compositions are disclosed herein, and it is understood that combinations, subsets, interactions, groups, etc. of these systems, apparatuses, methods and compositions are disclosed. That is, while specific reference to each various individual and collective combinations and permutations of these systems, apparatuses compositions and methods may not be explicitly disclosed, each is specifically contemplated and described herein. For example, if a particular system, apparatus, composition of matter or a particular method is disclosed and discussed and a number of systems, apparatuses, compositions or methods are discussed, each and every combination and permutation of the systems, apparatuses, compositions and the methods are specifically contemplated unless specifically indicated to the contrary. Likewise, any subset or combination of these is also specifically contemplated and disclosed.

Other aspects, advantages, and modifications are within the scope of the following claims.

What is claimed is:

1. A sample holder, comprising:
   a first substrate;
   a first member comprising a first aperture;
   a first retaining mechanism positioned on the first member, the first substrate secured on the first member by the first retaining mechanism;
   a second substrate;
   a second member comprising a second aperture;
   a second retaining mechanism positioned on the second member, the second substrate secured on the second member by the second retaining mechanism;
   a third substrate comprising a slide, a hydrogel, a porous membrane, or a flow cell;
   a base member comprising a third aperture and a fourth aperture;
   a third retaining mechanism positioned on the base member, the third substrate secured on the base member by the third retaining mechanism; and
   at least one hinge connecting the first and second members to the base member, wherein the first member and the second member each have an open configuration and a closed configuration with respect to the base member, wherein the at least one hinge is configured to allow relative movement of the first member and the second member relative to the base member, and wherein, when the first member is in the closed configuration, the first aperture is aligned with the third aperture and, when the second member is in the closed configuration, the second aperture is aligned with the fourth aperture.

2. The sample holder of claim 1, wherein the first substrate comprises a first sample comprising a first analyte in a first spatial arrangement and the second substrate comprises a second sample comprising a second analyte in a second spatial arrangement.

3. The sample holder of claim 1, further comprising one or more spacing members connected to at least one of the first member, second member, or the base member, the one or more spacing members positioned so that in the closed configuration, the one or more spacing members are between the first member and the base member, or between the second member and base member, or between the first member and the second member and the base member, or between the first substrate and the third substrate, or between the second substrate and the third substrate, or between the first substrate and the second substrate and the third substrate, and the one or more spacing members are configured to provide a minimum spacing between the first substrate and the third substrate, or between the second substrate and the third substrate, or between the first substrate and the second substrate and the third substrate.

4. The sample holder of claim 2, wherein the third substrate comprises at least one of a first array and a second array and in the closed configuration the first sample is vertically aligned with at least a portion of the first array of the third substrate and the second sample is vertically aligned with at least a portion of the second array of the third substrate.

5. The sample holder of claim 3, wherein the one or more spacing members form a chamber between the first substrate and the third substrate, or between the second substrate and the third substrate, or between the first substrate and the second substrate and the third substrate when the first and second members are in the closed configuration with respect to the base member.

6. The sample holder of claim 4, wherein in the closed configuration the third aperture or the fourth aperture is aligned with at least a portion of a sample region of the first substrate or at least the portion of the first array or the third aperture or the fourth aperture is aligned with at least a portion of a sample region of the first substrate and at least the portion of the first array.

7. The sample holder of claim 6, further comprising a reagent well formed by one or more bounding surfaces of the third aperture or the fourth aperture and by a first back surface of the first member or a second back surface of the second member, or by one or more bounding surfaces of the third aperture and the fourth aperture and by a first back surface of the first member and a second back surface of the second member, or by one or more bounding surfaces of the third aperture or the fourth aperture and by a first back surface of the first member and a second back surface of the second member, or by one or more bounding surfaces of the third aperture and the fourth aperture and by a first back surface of the first member or a second back surface of the second member, wherein a reagent solution added to the reagent well is contained by the bounding surfaces and travels from the reagent well to contact the first sample and/or the second sample when the first and second members in the closed configuration with respect to the base member.

8. The sample holder of claim 7, wherein the reagent well comprises a port configured to receive the reagent solution.

9. The sample holder of claim 8, wherein the port comprises a one-way valve.

10. The sample holder of claim 4, wherein the first aperture is aligned with at least a first portion of a first sample region of the first substrate, or the first aperture is aligned with at least a first portion the first array of the third substrate, or the first aperture is aligned with at least a first portion of a first sample region of the first substrate and at least a first portion the first array of the third substrate, and the second aperture is aligned with at least a second portion of a second sample region of the second substrate, or the second aperture is aligned with at least a second portion of the second array of the third substrate, or the second aperture is aligned with at least a second portion of a second sample region of the second substrate and at least a second portion of the second array of the third substrate.

11. The sample holder of claim 10, further comprising a first reagent well formed by one or more bounding surfaces of the first aperture and by a surface of the base member, wherein a reagent solution added to the first reagent well is contained by the bounding surfaces and travels from the first reagent well to contact the first sample when the first and second members are in the closed configuration with respect to the base member.

12. The sample holder of claim 11, wherein the first reagent well comprises a port configured to receive the reagent solution.

13. The sample holder of claim 7, wherein the base member comprises a fifth aperture in fluidic communication with the third aperture or a sixth aperture in fluidic communication with the fourth aperture, the fifth or sixth aperture configured to remove the reagent solution from the base member or the fifth and sixth aperture configured to remove the reagent solution from the base member.

14. The sample holder of claim 3, wherein the one or more spacing members comprise at least one of a first spacing member coupled to the first member, a first spacing member coupled to the first substrate, a first spacing member coupled to the first member and the first substrate, a second spacing member coupled to the second member, a second spacing member coupled to the second substrate, a second spacing member coupled to the second member and the second substrate, a third spacing member coupled to the base member, a third spacing member coupled to the third substrate, or a third spacing member coupled to the base member and the third substrate.

15. The sample holder of claim 14, wherein the first spacing member and the second spacing member comprises a thickness greater than the third spacing member.

16. The sample holder of claim 15, wherein the first substrate, the second substrate, the third substrate, the first spacing member, the second spacing member, and the third spacing member form a chamber when the first and second members are in the closed configuration with respect to the base member.

17. The sample holder of claim 16, wherein the chamber comprises a flow cell.

18. The sample holder of claim 1, wherein the base member comprises a removable portion, the removable portion including the third substrate.

19. The sample holder of claim 1, wherein the first substrate comprises a histology slide, the second substrate comprises a histology slide, or the first substrate and the second substrate comprise a histology slide.

20. The sample holder of claim 1, wherein the slide comprising an array.

21. A system comprising:
   the sample holder of claim 1; and
   a thermocycler.

22. The system of claim 21, wherein the sample holder is configured to be retained in the thermocycler.

23. A method of preparing biological samples for spatial analyses, the method comprising:
   providing a sample holder, wherein the sample holder comprises:
      a first substrate,
      a first member comprising a first aperture,
      a first retaining mechanism positioned on the first member, the first substrate secured on the first retaining mechanism,
      a second substrate,
      a second member comprising a second aperture,
      a second retaining mechanism positioned on the second member, the second substrate secured on the second retaining mechanism,
      a third substrate,
      a base member comprising a third aperture and a fourth aperture,
      a third retaining mechanism positioned on the base member, the third substrate secured on the third retaining mechanism, and
      at least one hinge connecting the first and second members to the base member, wherein the first member and the second member each have an open configuration and a closed configuration with respect to the base member,
   wherein the at least one hinge is configured to allow relative movement of the first member and the second member relative to the base member, and
   wherein, when the first member is in the closed configuration, the first aperture is aligned with the third aperture and, when the second member is in the closed configuration, the second aperture is aligned with the fourth aperture;
   securing at least one of the first substrate comprising a first biological sample in the first retaining mechanism of the first member, or the second substrate comprising a second biological sample in the second retaining mechanism of the second member, or the first substrate comprising a first biological sample in the first retaining mechanism of the first member and the second substrate comprising a second biological sample in the second retaining mechanism of the second member;
   via the at least one hinge, manually aligning the first member with the base member, or the second member with the base member, or the first and second members with the base member such that at least a portion of the first biological sample is vertically aligned with at least a first portion of a first array of the third substrate, or at least a portion of the second biological sample is vertically aligned with at least a second portion of the second array, or at least a portion of the first sample is vertically aligned with at least a first portion of a first array of the third substrate and at least a portion of the second biological sample is vertically aligned with at least a second portion of a second array when the first and second members are in the closed position relative to the base member; and
   migrating an analyte from the vertically aligned portion of the first biological sample to the first portion of the first array, or from the vertically aligned portion of the second biological sample to the second portion of the second array, or from the vertically aligned portion of the first biological sample to the first portion of the first array and from the vertically aligned portion of the second biological sample to the second portion of the second array.

* * * * *